United States Patent [19]
Walker et al.

[11] Patent Number: 5,672,498
[45] Date of Patent: Sep. 30, 1997

[54] HUMAN CORNEAL EPITHELIAL CELL LINES WITH EXTENDED LIFESPAN

[75] Inventors: Tracey L. Walker, Woodbridge, Va.; Carolyn R. Kahn, Woodbridge, Conn.

[73] Assignee: The Gillete Company, Boston, Mass.

[21] Appl. No.: 174,055

[22] Filed: Dec. 28, 1993

[51] Int. Cl.$^6$ .................................................. C12N 5/00
[52] U.S. Cl. ................................. 435/240.2; 435/7.21
[58] Field of Search ........................... 435/172.3, 320.1, 435/240.2, 7.21, 6

[56] References Cited

U.S. PATENT DOCUMENTS

| | | | |
|---|---|---|---|
| 4,707,448 | 11/1987 | Major | 435/240.25 |
| 4,760,020 | 7/1988 | Neufeld et al. | 435/29 |
| 4,808,532 | 2/1989 | Stampfer | 435/240.2 |
| 4,835,102 | 5/1989 | Bell et al. | 435/29 |
| 4,885,238 | 12/1989 | Reddel et al. | 435/29 |
| 5,374,515 | 12/1994 | Parenteau et al. | 435/1 |

OTHER PUBLICATIONS

Linder et al., *Exp. Cell Res.*, vol. 191, 1990, pp. 1–7.

*In Vitro Toxicity Testing*, edited by J.M. Frazier, "Draize Eye Irritation Test" p. 160.

"Cultured Epithelial Cells of Cornea, Conjunctiva and Skin: Absence of Marked Intrinsic Divergence of Their Differentiated States", Tung–Tien Sun et al, *Nature*, vol. 269, No. 5628, pp. 489–493, Oct. 6, 1977.

"Neoplastic Transformation of Human Epidermal Keratinocytes by AD12–SV40 and Kirsten Sarcoma Viruses", Johng S. Rhim et al, *Science*, Mar. 8, 1985, vol. 227, pp. 1250–1252.

"Characterization of Human Uroepithelial Cells Immortalized in Vitro by Simian Virus 40", Brian J. Christian et al, *Cancer Research* 47, 6066–6073, Nov. 15, 1987.

"Establishment and Characterization of SV40 T-Antigen Immortalized Human Esophageal Epithelial Cells", Stoner et al, *Cancer Research*, 51, 365–371, Jan. 1, 1991.

"Immortalization of Human Tracheal Gland Epithelial Cells by Adenovirus 12–SV40 Hybrid Virus", Letter to the Editor by Chopra et al, *In Vitro Cell Dev. Biol.* 27A:763–765, Oct. 1991.

"Cloning of cDNAs for Cellular Proteins that Bind to the Retinoblastoma Gene Product", D. Defeo–Jones et al, *Nature*, vol. 352, Jul. 18, 1991, pp. 251–254.

"Expression of SV–40 T Antigen in the Small Intestinal Epithelium of Transgenic Mice Results in Proliferative Changes in the Crypt and Reentry of Villus–associated Enterocytes into the Cell Cycle but Has no Apparent Effect on Cellular Differentiation Programs and Does Not Cause Neoplastic Transformation", Sherrie M. Hauft et al, *The Journal of Cell Biology*, vol. 117, No. 4, May 1992, pp. 825–839.

"In Vitro Test Validation: A House Built on Sand", Editorial, ATLA 20, pp. 196–198, 1992.

"Malignant Human Papillomavirus Type 16–transformed Human Keratinocytes Exhibit Altered Expression of Extracellular Matrix Glycoproteins", N. Sheibani et al, *Cancer Research* 51, 5967–5975, Nov. 1, 1991.

"Neoplastic Transformation of Human Epithelial Cells in Vitro", J. Rhim, *AntiCancer Research* 9, pp. 1345–1366, 1989.

"Isolation and Characterization of a Transformed Human Corneal Epithelial–Like Cell Line", H.V. Chaves et al., *Journal of Investigative Ophthalmology and Visual Science* vol. 32, No. 4, p. 1072, 1991.

"Generation and Morphological Characterization of Human Corneal Epithelial Primary Cultures and Immortalized Cell Lines in Serum Free Medium: Potential Model for Ocular Studies" C. Khan et al., *Journal of Investigation Ophthalmology and Visual Science* vol. 33, No. 4, p. 1176, 1992.

*Primary Examiner*—Mindy Fleisher
*Assistant Examiner*—James Ketter
*Attorney, Agent, or Firm*—Burns, Doane, Swecker & Mathis

[57] ABSTRACT

The present invention provides human corneal epithelial cell lines with extended lifespan. The cell lines are useful as an in vitro model of the human ocular surface. Methods for making and using the cell lines are also provided.

6 Claims, 17 Drawing Sheets

(6 of 17 Drawing(s) in Color)

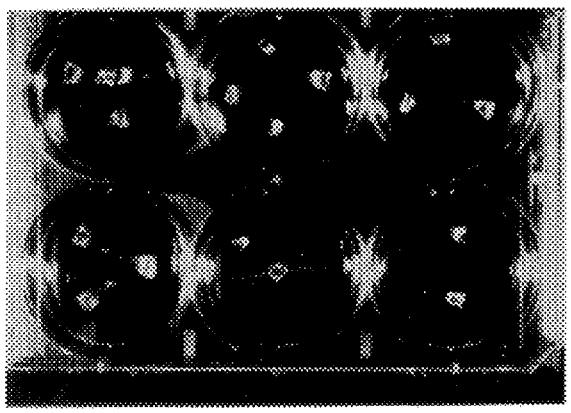
FIG. IA
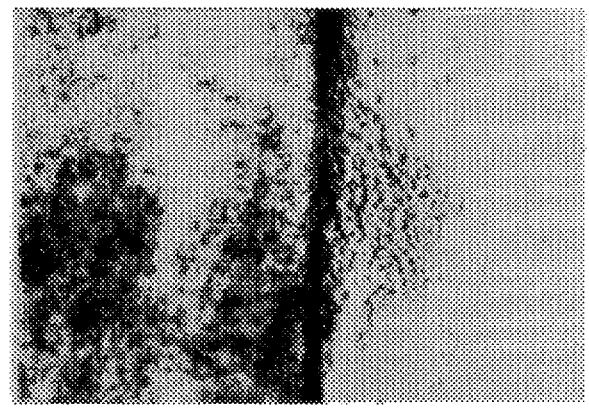
FIG. IB
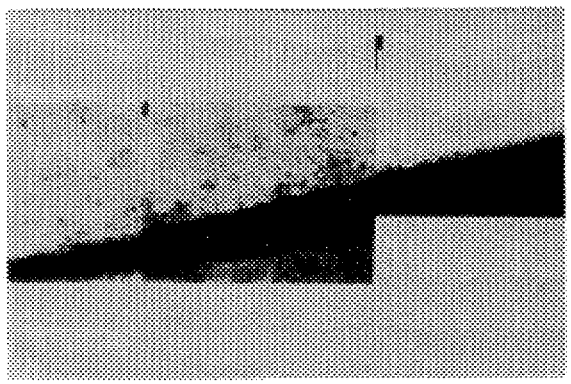
FIG. IC
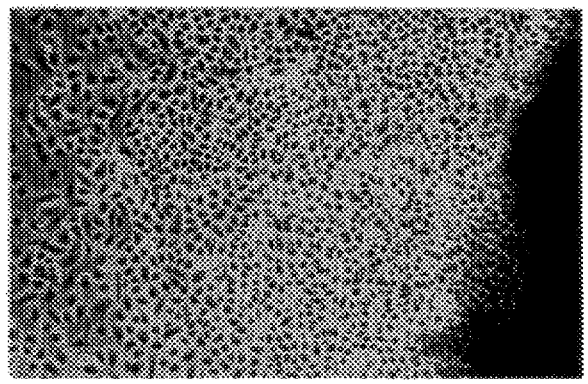
FIG. ID
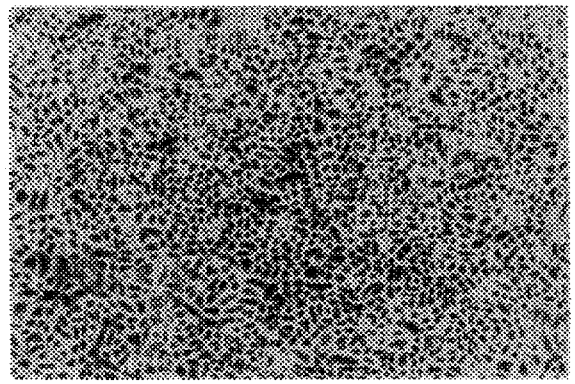
FIG. IE
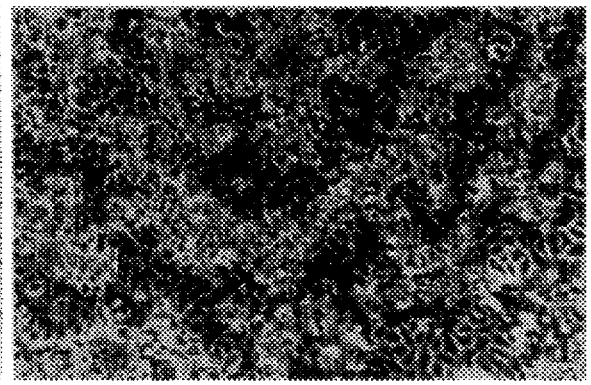
FIG. IF

| Cell Line | Highest Passage | Potential Yield | AE 5 | Vero - | Retention (%) | Retention Lost | Resistance (ohms cm$^2$) |
|---|---|---|---|---|---|---|---|
| HCE | 5 | 2.5 × 10$^8$ | + | na | 99 | P4 | 341 (+/- 329) |
| 50.A1 | 31 | | + | 7 | 93 | P19 | 84 (+/- 8) |
| 50.B1 | 31 | | +/- | 9 | 64 | | nd |
| D.91.139 | 29 | | - | *6 | 52 | | nd |
| 7.088 pRSV-T | 14 | | | na | nd | | nd |
| 7.107 pRSV-T | 15 | | + | na | 76 | P9 | nd |
| 7.107 pSV3neo | 12 | | | na | nd | | nd |
| 42 | 7 | | | *6 | nd | | nd |
| 46 (1:10) | 12 | | | 12 | nd | | nd |
| 72 (1:10) | 5 | | | *5 | nd | | nd |
| 62 (1:10) | 9 | | | *9 | nd | | nd |
| 5.099.1A | 27 | | + | *27 | nd | | nd |
| 8.002 pRSV-T | 6 | 1.3 × 10$^8$ | | na | nd | | nd |
| 8.048 pRSV-T | 9 | 2.4 × 10$^8$ | | na | nd | | nd |
| 8.094 pRSV-T | 15 | 4.0 × 10$^{11}$ | + | na | 95 | P14 | 139 (+/- 35) |
| 9.021 pRSV-T | 18 | 2.0 × 10$^{13}$ | +/- | na | 94 | P17 | 105 (+/- 31) |
| 9.069 pRSV-T | 16 | 2.9 × 10$^{12}$ | +/- | na | 97 | P15 | 160 (+/- 63) |
| 9.073 pRSV-T | 9 | 1.4 × 10$^9$ | + | na | 73 | | nd |
| 9.097 pRSV-T | 12 | 1.4 × 10$^7$ | | na | 69 | | nd |
| 10.001 pRSV-T | 5 | | | na | nd | | nd |
| 10.014 pRSV-T | 24 | 1.6 × 10$^{15}$ | + | na | 98 | P22 | 238 (+/- 79) |
| 1.069 pRSV-T | 13 | 5.7 × 10$^{10}$ | + | na | 99 | P13 | 532 (+/- 31) |
| 2.018 pRSV-T | 8 | | | na | 43 | | nd |
| 2.040 pRSV-T | 21 | 1.6 × 10$^{13}$ | + | na | 96 | P20 | 172 (+/- 19) |
| PRG.92.03.041 (HSF) | 21 | | | na | 22 | | 1 (+/- 1) |
| SIRC | na | | + | na | 67 | | 26 (+/- 11) | na = not applicable
nd = not done
* = still Vero + at this passage number
HSF = human stromal fibroblasts

FIG. 13

HUMAN CORNEAL EPITHELIAL CELL LINES WITH EXTENDED LIFESPAN

BACKGROUND OF THE INVENTION

1. Field of the Invention

The present invention is directed to the production of immortalized human corneal epithelial cell lines with improved properties and their use.

2. Description of the Related Art

The corneal epithelium provides the characteristic epithelial barrier for the eye. It is a transparent barrier which also aides in maintaining the transparency of the underlying corneal stroma. The transparency allows light penetration to the retina and is crucial to visual acuity. Injury of the corneal epithelium may result in the loss of sight. Accordingly, to protect against inadvertent damage from commercially applied materials, the Food, Drug and Cosmetic Act of 1938 has required testing of cosmetic and drug products.

The current method for testing ocular irritancy in humans employs the use of rabbits. The method involves placing a foreign substance directly into the conjunctival sac of the rabbit eye. This assay is known as the Draize Test. The Draize Test is simple to perform, allows a quick economical result and uses a laboratory animal which is easy to breed and maintain. The test is described in Draize et al, 1944, *J. Pharmacol. Exp. Ther.*, Vol. 82, pp. 377–390. However, there are drawbacks to the use of the Draize Test. First, there are morphological and biological differences between the laboratory animal eye and the human eye. See, for example, Goldberg, A. M. Ed., Alternative Methods in Toxicology: A Critical Evaluation of Alternatives to Acute Ocular Irritation Testing, Mary Ann Liebert, Inc., 1987. Secondly, in vitro models must satisfy several stringent criteria in order to be informative, including species and tissue specificity, which are key in order to determine specific biochemical and tissue specific mechanisms. Furthermore, animal rights groups adamantly protest against the use of animals in experimental research.

In vitro models for human corneal epithelium that utilize continuous cell lines have been proposed for toxicology studies. These models include the SIRC cell line (rabbit origin) which has a fibroblast morphology (Neiderkorn et al, 1990, *In Vitro Cell Dev. Biol.*, Vol. 26, pp. 923–930) and the MDCK (Madin-Darby canine kidney) line (*American Type Culture Collection. Catalog of Strains*. 6th Ed., 1988, p. 21).

Alternatives to animal models have been proposed and human corneal organ culture techniques have been developed. See, for example, Doughman, D. J., 1980, *Trans. Am. Ophthalmol. Soc.*, LXXCVIII, pp. 527–628; Richard et al, *Current Eye Research*, 1991, Vol. 10, pp. 739–749. In fact, primary cultures of human corneal epithelium have been used to model the ocular surface in vitro. See, Newsome et al, *Invest. Ophthal.*, 1974, Vol. 13, p. 23; Ebato et al, *Invest. Ophthal. and Vis. Sci.*, 1987, Vol. 28, pp. 1450–1456; and Hainsworth et al, *Tissue Culture Methods*, 1991, Vol. 13, pp. 45–48. However, primary cultures, even when maintained with fetal bovine serum, fibroblast feeder layers or growth supplements, become senescent after several passages in vitro. Thus, such cultures have a restricted finite life-span. In addition, not only is there biological variability among individual donors, but the availability of donor corneal material is uncertain.

There is therefore a need in the art for a substantially stable, continuous human corneal epithelial cell line. Such a cell line would be useful in the study of the effects of chemicals and drugs on the human eye as well as in basic research on the human eye. In addition, there is also a need for producing such a cell line which has an extended lifespan, and which maintains morphological properties similar to that of the primary cells. The present invention addresses these needs by providing such cell lines derived from human corneal epithelial cells.

SUMMARY OF THE INVENTION

The present invention is drawn to continuously growing or immortalized human corneal epithelial cell (HCE-T) lines. The cell lines retain their phenotypic differentiation and response to external regulatory and growth stimuli. That is, the cell lines can be maintained in culture for an increased period as continuous stable cell lines. They can be grown in three dimensional structures to model corneal epithelium in vitro, thus providing a system with the potential to test water soluble and solid products. Moreover, the cells retain morphological characteristics similar to that of the primary cells from which they are derived.

Accordingly, a major object of the present invention is to provide human corneal epithelial cell (HCE-T) lines with extended lifespan.

Another object of the invention is to provide an in vitro model of the human ocular surface.

A further object of the invention is to provide methods for making and using the cell lines.

In a first aspect, the present invention relates to a method for producing an immortalized human corneal epithelial cell line which includes (a) culturing human corneal cells, (b) infecting the cells with a virus capable of infecting the corneal cells, or transfecting the cells with a plasmid capable of transfecting the corneal cells, such that the cells become continuously growing and, (c) recovering the continuously growing corneal cells.

In a second aspect, the present invention relates to continuous, stable, human corneal epithelial cells lines.

In a third aspect, the present invention relates to a method for determining the effect of a chemical or drug on the eye by (a) contacting an immortalized human corneal epithelial cell line with the chemical or drug, and (b) determining the effect of the chemical or drug on the cell culture.

With the foregoing and other objects, advantages and features of the invention that will become hereinafter apparent, the nature of the invention may be more clearly understood by reference to the following detailed description of the preferred embodiments of the invention and to the appended claims.

The file of this patent contains at least one drawing executed in color. Copies of this patent with color drawing(s) will be provided by the Patent and Trademark Office upon request and payment of the necessary fee.

BRIEF DESCRIPTION OF THE DRAWINGS

FIG. 1 shows primary cultures generated from explanted donor cornea. FIG. 1A shows an explanted pair of donor corneas attached to culture substrate. FIG. 1B shows epithelial outgrowth seen after 24 hours in culture. FIG. 1C shows epithelial outgrowth occurring from the limbal area of the cornea (sclera to the right and central cornea to the left). FIG. 1D shows epithelial outgrowth remaining attached after removal of the donor tissue slice on culture day 5. FIG. 1E shows a confluent epithelial culture seen 2 weeks after donor was explanted. FIG. 1F shows a post-confluent culture.

* a) confluent HCE b) post-confluent HCE c) confluent HCE-T d) post-confluent HCE-T FIG. 3 illustrates growth kinetics.

FIG. 4 shows a donor cornea eye bank history related to frequency of primary cultures.

FIG. 5 shows human corneal epithelial cultures six weeks after T transfection.

FIG. 6 shows paraffin embedded, H & E stained slices of HCE-T.

FIG. 7 shows a karyotype analysis of two lines developed from the same donor.

FIG. 8 shows the growth characteristics of HCE (control) vs. 5 different HCE-T.

FIG. 9 shows immunofluorescence profiles of HCE-T.

FIG. 10 shows the effect of fetal bovine serum (FBS) on HCE-T morphology.

FIG. 11 shows corneal derived cells with non-epithelial morphology.

FIG. 13 is a summary of characteristics of various transformed HCE-T lines, in comparison to the untransformed HCE cells.

FIG. 14 are photomicrographs demonstrating the morphological similarity between HCE and cell line 10.014 pRSV-T.

DETAILED DESCRIPTION OF THE PREFERRED EMBODIMENTS OF THE INVENTION

Figure 2A:
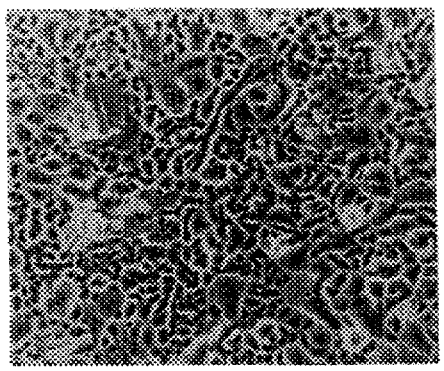
FIG. 2 is a human corneal epithelial (HCE) primary culture morphology compared to a T transfected human corneal epithelial (HCE-T) line.*

Cells useful for the present invention can be derived from any human donor corneas, regardless of age or tissue type. Preferably, donor corneas have been determined to be uninfected by any virus, especially hepatitis B, hepatitis C or human immunodeficiency virus (HIV).

Cells may be derived from the corneal tissue by any method known in the art, but are preferably derived by a means which results in minimal damage to the collagen matrix, and in liberation of fibroblasts. Cells derived by explant are preferable. A preferred method involves culturing the donor corneas epithelial side down in a culture medium which will maintain the corneal cells, preferably in a serum-free medium, and preferably in a medium containing growth factors which stimulate the growth of the corneal cells. Such growth factors may include bovine pituitary extract, epidermal growth factor and hydrocortisone. Particularly preferable growth factors include epidermal growth factor and bovine pituitary extract. The cultures are incubated with adequate medium changes. By adequate medium changes, it is intended that the medium changes occur at least twice weekly.

At about 70–80% confluence, cells are collected and plated onto tissue culture surfaces. Cells may be grown on any tissue culture flask or plate, but preferable surfaces are those which have been coated with substances resembling the extracellular matrix, such as fibronectin and collagen. General methods of cell culture can be found in *Neoplastic Transformation in Human Cell Culture: Mechanisms of Carcinogenesis*, 1991, Rhim et al, eds., Humana Press, Totowa, N.J. and *Culture of Epithelial Cells*, 1991, Freshney, R. I., ed., A. John Wiley and Sons, Inc., New York, N.Y., which disclosures are herein incorporated by reference.

Cells are passaged by removing them from the tissue culture surface by any means, washing, resuspending in tissue culture medium and plating onto a tissue culture surface. A particularly preferable means of removing the cells from the tissue culture surface is with the use of trypsin-ethylenediaminetetraacetic acid (EDTA). The cells may be washed with any sterile medium or solution, including phosphate buffered saline.

The cells are then "immortalized" using a virus or plasmid which contains nucleic acid capable of transforming the cells to a continuously growing state. Immortalization as used herein refers to a process which increases the lifespan of a cell, particularly a primary cell, so that the resulting cell line is capable of being passaged many more times than the primary cell is capable of being passaged.

Any virus may be used to transform the cells which contains a transforming nucleic acid sequence, and can extend the lifespan of the cells. Such viruses include papilloma viruses, SV40 viruses, and hybrid viruses containing SV40 transforming genes, such as Adeno12-SV40. These viruses express SV40 T antigen, which is a multi-functional transforming protein that binds p53 and Rb gene product, but any molecule that binds to p53 theoretically could be employed to achieve the same end. T antigen contains a domain that has been identified in adenovirus E1A.

Alternatively, plasmids may be used to transfect the cells with nucleic acid capable of transforming the cells. Such plasmids may include sequences from SV40 virus, such as RSV-T (pRSV-T), sequences from papilloma viruses, or any other transforming sequences.

SV40-based viruses are preferable for carrying out the present invention. The SV40 virus and methods for obtaining the virus and vital DNA have been described in the literature. See, for example, Rhim et al, 1981, *Proc. Natl. Acad. Sci.*, Vol. 78, pp. 313–317; Rhim, *Anticancer*

*Research*, 1989, Vol. 9, pp. 1345–1366; and Rhim et al, *Science*, 1985, Vol. 227, pp. 1250–1252.

SV40-based plasmids are also preferable for use in the present invention. Particularly preferable is the plasmid pRSV-T, the use of which is described in Reddel et al, 1988, *Cancer Research*, Vol. 48, pp. 1904–1909. This plasmid contains the SV40 early region genes and the Rous Sarcoma Virus long terminal repeat.

Infection of the cells by the SV40 virus, or transfection of the cells with a plasmid containing SV40 sequences can be confirmed by assaying for the presence of SV40 antigens. Such assays may include the use of polyclonal or monoclonal antibodies to SV40 antigens.

The immortalized cell lines of the invention cease to shed virus into the culture supernatant and are capable of culture for an extended period of time. They are also capable of developing into confluent monolayers on plastic surfaces. Such lines can be maintained in culture or frozen in liquid nitrogen and recovered later as viable cells.

The cell lines can be tested to assure that they retain the phenotypic traits of human corneal epithelial cells. Such characteristics which can be tested include, for example, morphology, saturation density, population doubling time, karyotype and specific cytokeratin synthesis. Morphological studies can be conducted using methods of microscopy such as phase-contrast and brightfield microscopy. Saturation density and population doubling time can be analyzed by releasing cells from a tissue culture surface, and counting cells by any means, particularly by the use of a Coulter counter.

The karyotypes of the immortalized cell lines are hyperdiploid, which is typical of virally immortalized lines. Methods of karyotype analysis are well known in the art, and are preferably conducted on multiple Giemsa-banded chromosome spreads. Further characterization of the lines includes confirmation of the human origin of the lines by isozyme profile. Any enzymes may be analyzed whose isozyme profile is known. Particularly preferable enzymes include lactate dehydrogenase (LDH), glucose-6-phosphate dehydrogenase (G6PD), purine nucleoside phosphorylase (NP), malate dehydrogenase (MDH), mannose phosphate isomerase (MPI), aspartate aminotransferase (AST), peptidase B (PEPB), phosphoglucomutase-1 (PGM1), phosphoglucomutase-3 (PGM3), esterase D (ESD), malic enzyme, mitochondrial (Me-2), adenylate kinase (AK-1), glyoxylase-1 (GLO-1) and the like.

In addition to the above properties, a measurement of the resistance of the cells can provide an indication that the cells have retained morphology and characteristics similar to those of the parent primary cells.

The cell lines of the invention are useful in a variety of methods. Such methods include a model system for the human ocular surface. Such a model is useful for toxicity testing. For toxological applications of the cell lines, see, *A Critical Evaluation of Alternatives to Acute Ocular Irritation Testing*, 1987, Frazier et al, eds., Mary Ann Liebert, Inc., New York, N.Y. Furthermore, the cell lines can be utilized as model systems to experiment on wound healing of the human cornea, host-parasite interactions, radiation biology, genetic engineering, models to test the treatment of drugs and cosmetics, and as a model system for viral infection and diseases of the eye, etc.

Other useful aspects of the immortalized cell lines are that they synthesize both the 92 kD and 72 kD species of collagenase, as do control cultures, and that both control cultures and HCE-T can be infected with HIV in vitro.

The following examples are presented in order to more fully illustrate the preferred embodiments of the invention. They should in no way be construed, however, as limiting the broad scope of the invention.

EXAMPLE 1

Culturing of Human Corneal Cells

Human donor corneas, previously found to be non-reactive to Hepatitis B, Hepatitis C and HIV, and stored in Optisol, McCarey-Kauffman or Dexsol storage media at 4° C., were obtained from the Maryland Eye Bank Baltimore, Md.). No restrictions were placed on the age of the donor. Donor age ranged from 3 months to 86 years (mean=46 years±22), time between death, and preservation of the cornea ranged from 2 hours to 2 days (mean=9 days±7).

Donor corneas were placed epithelial side up on a sterile surface and cut into 12 triangular-shaped wedges, using a single cut of the scalpel, avoiding any sawing motion. Careful handling of the cornea in this manner decreases damage to the collagen matrix of the stroma and prevents liberation of fibroblasts. Each corneal segment was turned epithelial side down (FIG. 1a), and four segments were planted in each well of a six-well tray (precoated with rat-tail collagen, type I, Biocoat, Collaborative Research, Bedford, Mass.). Each segment was gently pressed down with forceps to ensure good contact between the tissue and the tissue culture surface. The tissue was allowed to dry for 20 minutes. One drop of antibiotic and serum-free medium (Keratinocyte Growth Medium, Clonetics, San Diego, Calif.) containing 0.15 mM calcium, human epidermal growth factor (0.1 ng/ml), insulin (5 µg/ml), hydrocortisone (0.5 µg/ml) and bovine pituitary extract (30 µg/ml) was carefully placed upon each segment and the tissue was allowed to incubate overnight (37° C., 5% $CO_2$). Although the donor corneas received from the eye bank were stored in antibiotic-containing medium (either Optisol, McCarey-Kauffman or Dexsol), all subsequent manipulations were performed under antibiotic-free conditions. The following day, one ml of medium was added to each well.

On day 5 the tissue segment was removed with forceps, and 3 ml of medium was added. Following this initial outgrowth period, cultures were fed 2 times per week. These cultures were denoted $P_0$. After 5 days, corneal tissue was removed, adherent cells continued to proliferate, and, within 2 weeks from the time of establishment of the culture, approximately $3 \times 10^6$ cells/cornea were harvested. At 70–80% confluence, cells were rinsed in Dulbecco's phosphate-buffered saline (D-PBS) and released with trypsin-ethylene dime tetraminic acid (EDTA) (0.05% trypsin, 0.53 mM EDTA, Gibco, Grand Island, N.Y.) for 4 minutes at 37° C. The reaction was stopped with 10% fetal bovine serum (FBS) in D-PBS). Cells were washed, resuspended and plated at $1 \times 10^4$ cells/cm$^2$ onto tissue culture surfaces which had been previously coated with a solution of commercially prepared fibronectin and collagen (FNC, Bethesda Research Faculty and Facility, Ijamsville, Md.). The fibronectin/collagen solution consists of fibronectin (10 mg/ml), collagen (35 µg/ml) and bovine serum albumin (BSA, 100 µg/ml) added as a stabilizer. These cultures were denoted passage 1 ($P_1$). Control cultures could be expanded until $P_5$, which represents approximately 9–10 population doublings. Senescence for control cultures ensued between P3 and P5, depending on the culture.

One day after trypsinization and reseeding, culture medium was exchanged with fresh medium. When $P_1$ cultures become 70–80% confluent they were subpassaged and designated $P_2$. Unless otherwise noted, keratinocyte serum-free medium was used throughout and all culture plasticware was coated with FNC immediately prior to addition of cells. All incubations occurred at 37° C. 95% air, 5% $CO_2$.

Cryopreservation was conducted by pelleting trypsin-dispersed cells at 60 g×5 minutes, resuspending in FBS containing 10% dimethylsulfoxide (DMSO, Sigma, St Louis, Mo.), aliquoting at 1–2×10$^6$ cells/cryovial, and freezing at a rate of 1° C./minute using a controlled temperature freezing apparatus (Forma, Marietta, Ohio). Cryopreserved cells were recoverable as viable cells with a 70–80% seeding efficiency, identical to that of trypsinized cells that have not experienced cryopreservation. Cryopreserved cells require about 2 days to resume normal growth rates.

HCE-T cell culture supernatants were monitored for mycoplasma contamination using a commercial assay (Gibco, Grand Island, N.Y.) and 3T6 cells (American Type Culture Collection, Rockville, Md.) as recommended by the manufacturer. Briefly, adenosine phosphorylase, which is synthesized by mycoplasma, converts 6-methylpurine deoxyriboside into a metabolite which is toxic to mammalian cells. All of the HCE-T cultures were determined to be negative for mycoplasma contamination as evidenced by the confluent lawns of 3T6 fibroblasts remaining after their co-culture with supernatants derived from each of the HCE-T lines.

EXAMPLE 2

Hybrid Virus Infection of Corneal Cells

Ad12-SV40 virus was grown in Green Monkey Kidney (Vero) cells as described previously (Rhim et al, 1981, *Proc. Natl. Acad. Sci.* Vol. 78, pp. 313–317). Primary cultures at $P_1$ obtained from a single donor, were grown to 60% confluence in 4 individual T-25 flasks. Three flasks were inoculated with Ad12-SV40 hybrid virus at a multiplicity of infection of approximately 100. Each dilution of virus was prepared in 5 ml of keratinocyte growth medium (KGM). The control flask was inoculated with medium only. Cells were incubated overnight with virus at 37° C., and the medium was exchanged the following day and twice weekly thereafter. Cultures were passaged as they approached confluence, 2 to 5 days after inoculation.

Figure 5A:
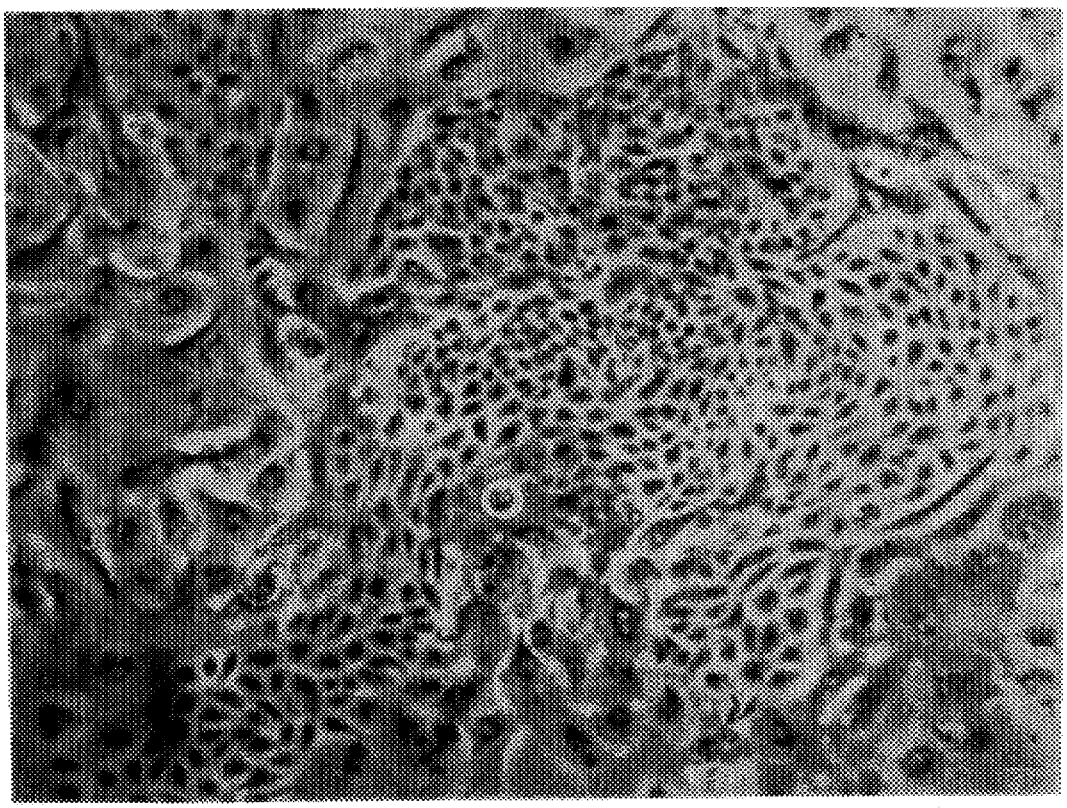
FIG. 5A is colonies of tightly packed epithelial cells in a T transfected flask.
Figure 5B:
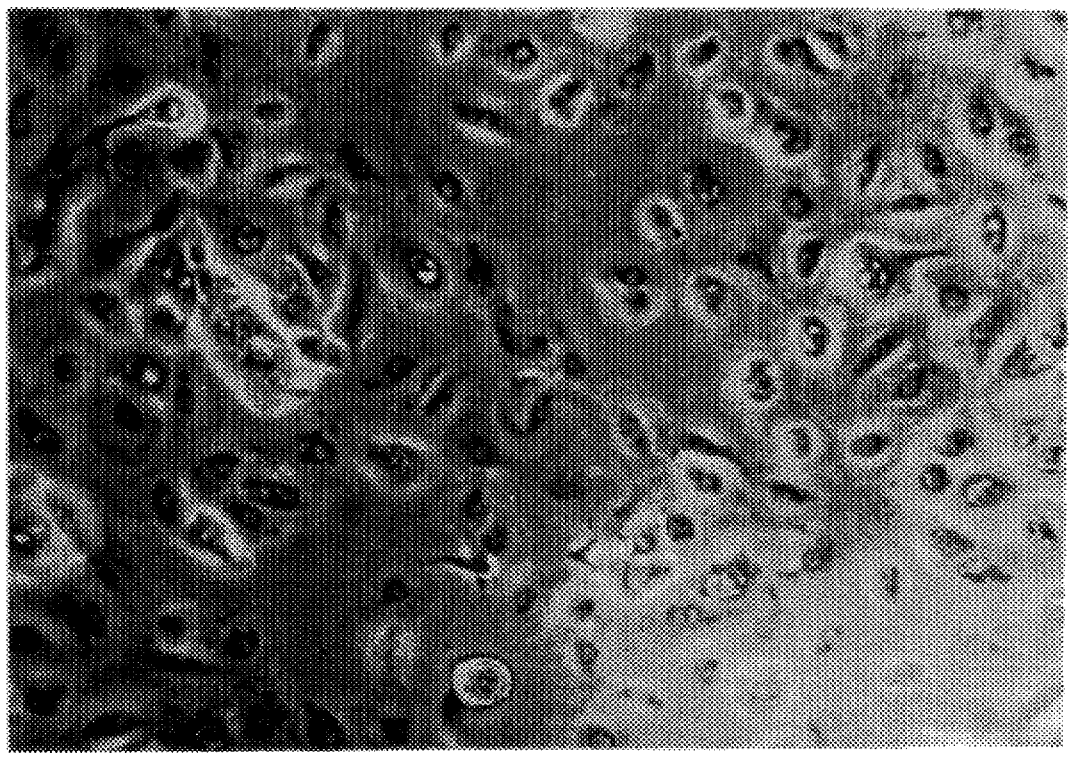
FIG. 5B is a sham transfected control culture.

Foci, as detected by phase contrast photomicroscopy, appeared in the inoculated flash between 4–6 weeks post-inoculation (FIG. 5a). Actively growing cultures were sub-cultured by trypsinization when the control cultures were senescent. Control cultures always senesced by the fifth passage (FIG. 5b) while Ad12-SV40-infected cultures exhibited extended lifespan (FIG. 5a).

An example of a cell line produced by the infection with this hybrid virus is cell line 50.B1, deposited with the American Type Culture Collection (ATCC), 12301 Parklawn Drive, Rockville, Md. 20852, USA on Sep. 23, 1992, and given ATCC deposit number CRL11135.

EXAMPLE 3

Transfection of Corneal Cells

Plasmid RSV-T (pRSV-T) (a gift from Dr. J. Brady and Dr. B. Howard, National Cancer Institute) is an SV40 ori-construct containing the SV40 early region genes and the Rous sarcoma virus long terminal repeat. The plasmid was amplified and banded twice in cesium chloride (Lofstrand Labs, Gaithersburg, Md.). Primary or secondary cultures of corneal epithelial cells ($P_1$ or $P_2$) were transfected by lipofection in 25 cm$^2$ flash by the method of Felgner et al (1987, *Proc. Natl. Acad. Sci.*, Vol. 84, pp. 7413–17). Briefly, Lipofectin (Gibco BRL, Grand Island, N.Y.) (30 µg/50 µl distilled water) was mixed 1:1 with plasmid DNA (10 µg/50 µl distilled water) in polystyrene tubes. After gentle agitation, the mixture was allowed to stand at room temperature for 15 minutes. Five ml of medium was added to the flask and 0.1 ml of mixture was added dropwise to each T-25 flask of epithelial cells. Flasks were incubated overnight at 37° C. at which time medium was exchanged. Cultures were fed twice weekly thereafter. Control cultures received Lipofectin only.

Morphologically, lines developed by transfection with plasmids and containing the early region SV40 genes were indistinguishable from the virally infected lines.

Examples of cell lines produced by transfection are cell line 7.107, deposited with the ATCC on Sep. 23, 1992, and given ATCC deposit number CRL11136, and cell lines 2.040 and 10.014, deposited with the ATCC on Dec. 28, 1993, and given ATCC deposit numbers CRL11516 and CRL11515, respectively (American Type Culture Collection (ATCC), 12301 Parklawn Drive, Rockville, Md. 20852, U.S.A.)

EXAMPLE 4

Examination of Morphology of Transformed Cells

Cells were examined using phase-contrast and brightfield microscopy with a Zeiss ICM 405 microscope equipped with a Nikon 35 mm camera and a Polaroid 4×5 format camera.

During the initial 24 hour culture period, emigration of cells could be observed only from the limbal region of the cornea (FIG. 1b). No cells were observed to migrate away from the central cornea or the sclera over the first 48 hours (FIG. 1c). The leading edge or most peripheral cells were stellate and highly migratory but where the cultures were dense, they formed a cobblestone monolayer as clearly seen by day 5 (FIG. 1d). By utilizing a serum-free medium low in calcium (0.15 mM), minimizing disruption of the collagen matrix, and leaving donor tissue in vitro for no longer than 5 days, fibroblast outgrowth was minimized.

Figure 2B:
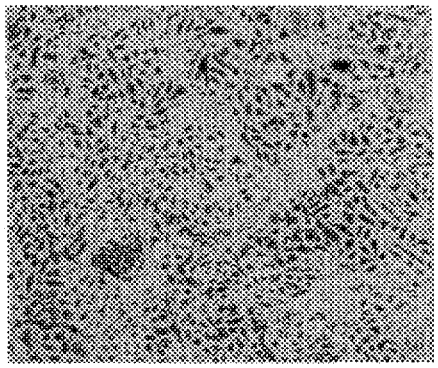

After corneal tissue was removed, adherent cells continued to proliferate and within 2 weeks from the time of establishment of the culture, confluent monolayers formed displaying the typical cobblestone morphology associated with epithelia (FIG. 1e). These cultures were denoted $P_0$. Approximately 3×10$^6$ cells/cornea were produced from each $P_0$ culture. Primaries allowed to propagate past confluence stratified in discrete areas over the confluent monolayer (FIG. 1f). Phase contrast photomicroscopy demonstrated that control cultures and HCE-T develop into confluent monolayers on plastic substrates (SD=1–2×10$^5$ cells/cm$^2$) (FIGS. 2a,c). Stratification could often be detected in early passage control cultures as raised areas of cell growth on a cobblestone monolayer in post-confluent submerged cultures (FIG. 2b).

Primary cultures were routinely passaged at 1×10$^4$ cells/cm$^2$ (5% confluence) and designated $P_1$. Immediately after passage, cells appear more spindle shaped, were refractile and highly migratory, but within a week they develop into a cobblestone monolayer. Giant cells were present and cultures were not as uniform in appearance as the $P_0$ cultures (FIG. 2a). When $P_1$ cultures become 70–80% confluent, they were subpassaged and designated $P_2$. Early passage cultures derived from donor cornea continue to display a cobblestone morphology, and if allowed to become post-confluent, the cultures retained the ability to stratify in discrete areas (FIG. 2b), but after $P_3$, the ability to stratify was lost.

Figure 2C:
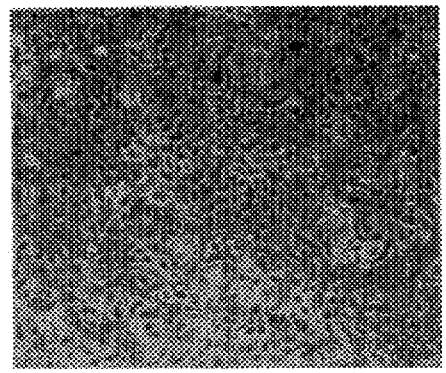
Figure 2D:
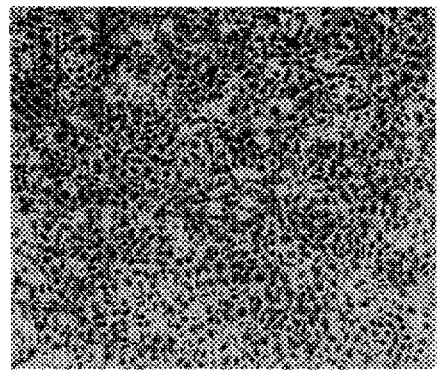

In vitro transformed HCE-T lines also appear stellate and highly migratory when plated at $1\times10^4$ cells/cm$^2$ and they also develop into confluent monolayers (FIG. 2c). Similar to the later passage control cultures, they no longer exhibit the ability to stratify in discrete areas even when allowed to become highly post-confluent; rather the cells become very tightly packed on the surface of the plastic substrate (FIG. 2d).

Figure 3A:
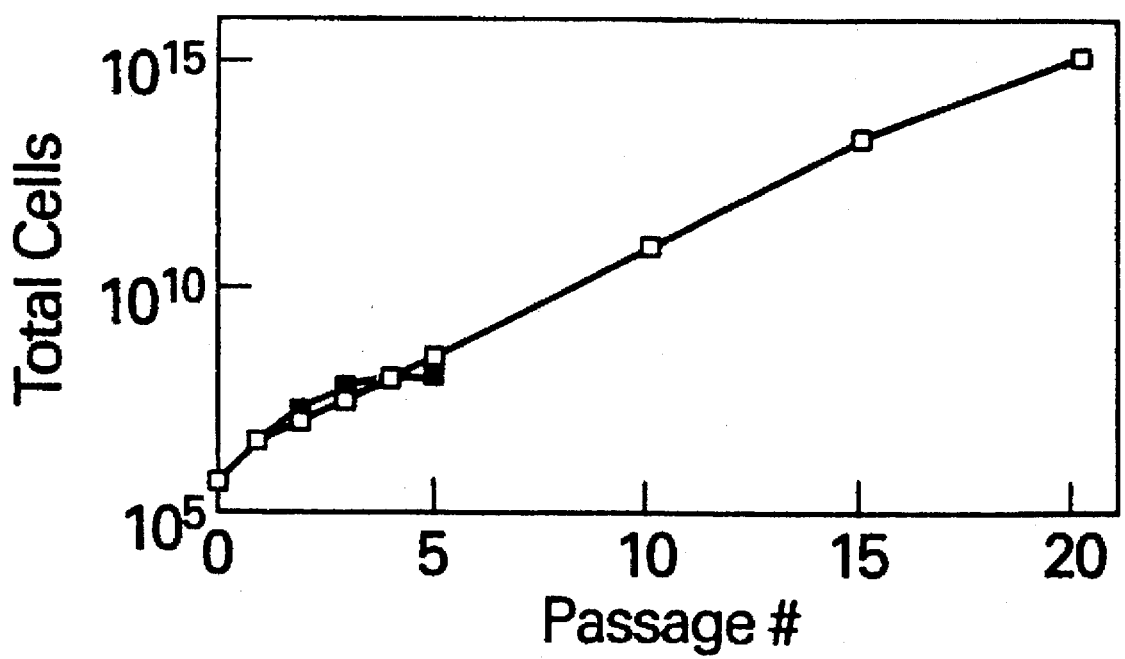
FIG. 3A is a comparison of potential cell yields from one donor cornea that is serially propagated, HCE (closed squares) versus one donor cornea that is T transfected, HCE-T (open squares).
Figure 3B:
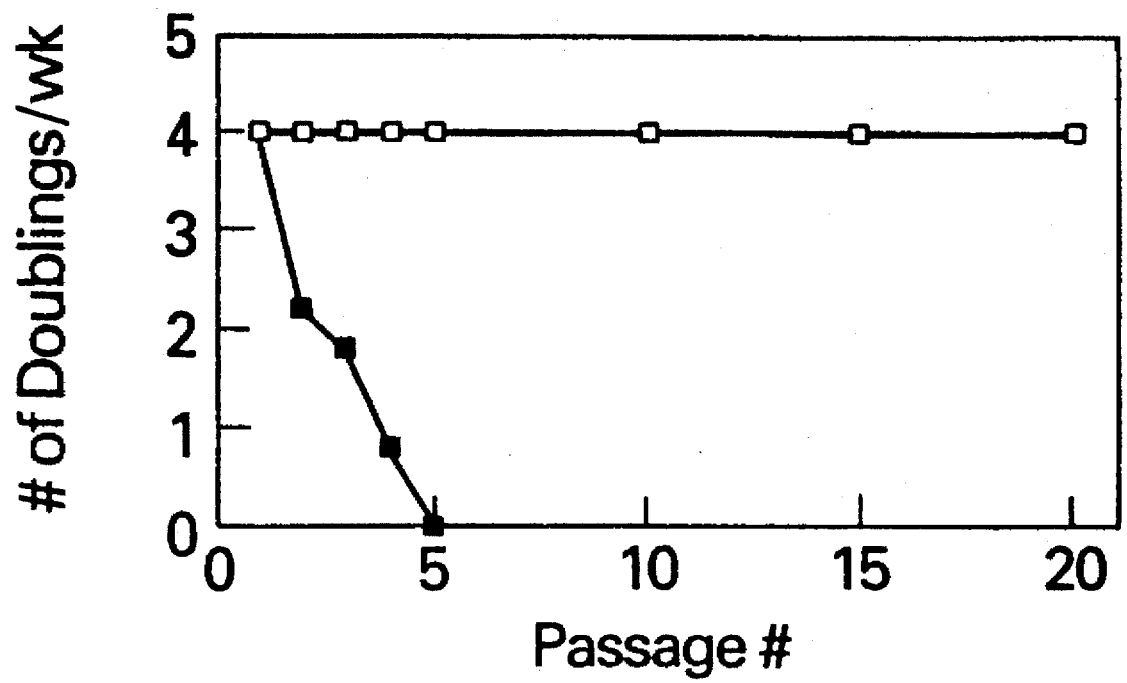
FIG. 3B shows that HCE lose the potential to double while HCE-T are stable for 20 serial passages.

Although control cultures could be expanded until $P_5$ (approximately 9–10 population doublings), most of the proliferation occurred between passages one and three (FIG. 3a). Approximately $125\times10^6$ cells/cornea could be generated, yielding a 20 fold amplification in cell number. Senescence always ensued by $P_5$ in control cultures. In contrast, HCE-T had a constant rate of passage (FIG. 3b) over at least 20 passages, and a $1\times10^9$ amplification of the starting population could be achieved. Since the starting population of cells was generally several million, quite large population of HCE-T could be generated in this manner.

Figure 4A:
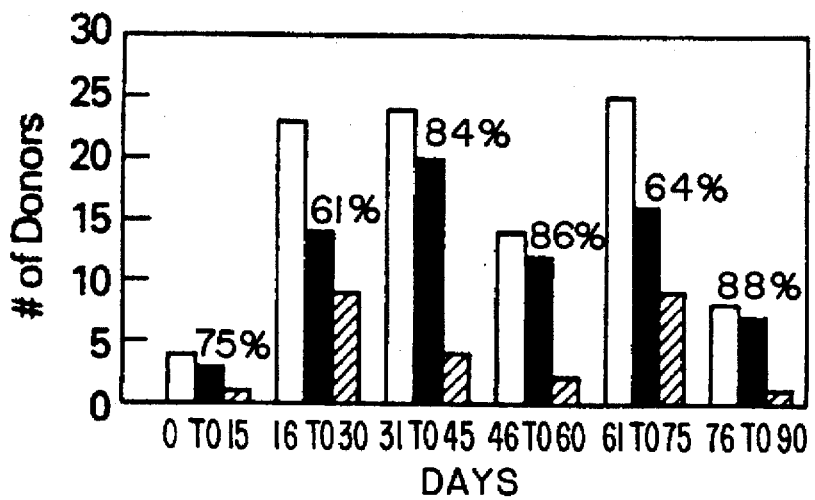
FIG. 4A is an explanted cornea producing a primary outgrowth independent of the donor age (years).
Figure 4B:
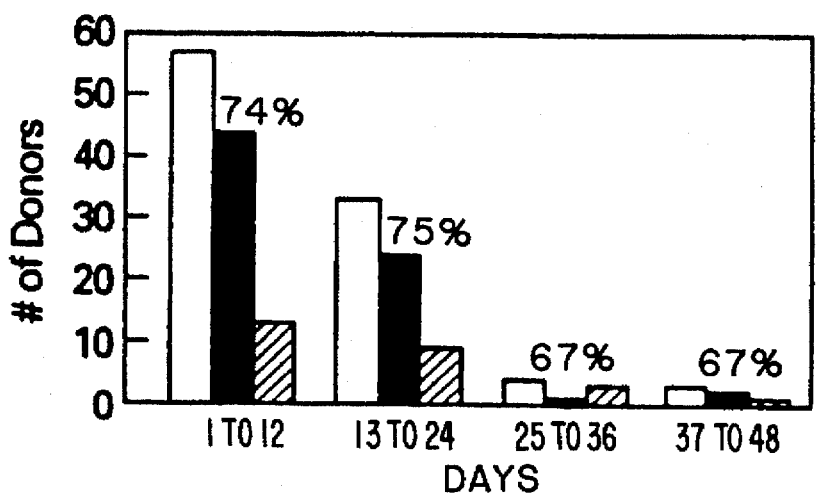
FIG. 4B is the time (hours) between death of the donor and excision of the cornea.
Figure 4C:
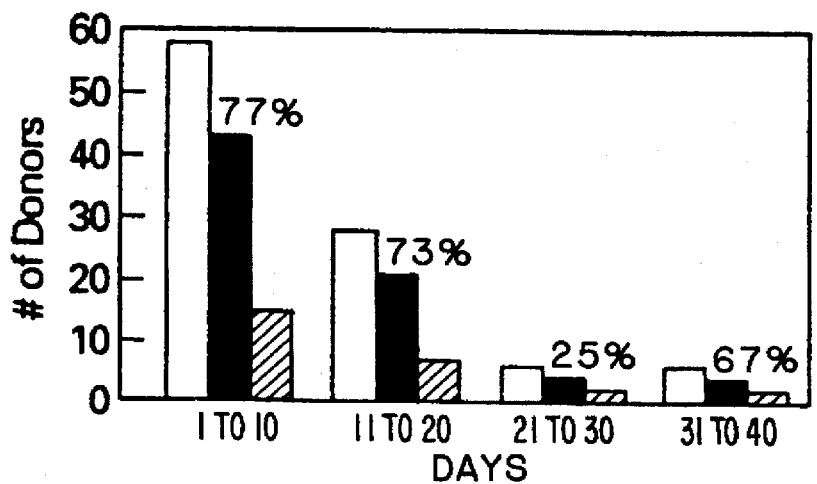
FIG. 4C is the time (days) the corneas are stored in the eye bank prior to explanation.

Age of the organ donor (mean age=47 years±22, range=4 months to 86 years), time between death of the donor and time of storage of the cornea (up to 48 hours post mortem) and the length of storage in the eye bank (up to 20 days) did not appear to affect the ability of the epithelial cells to initiate cultures (n=88) (FIG. 4a–c). Of the donors processed, 72/104 or 69% yielded successful corneal primary cultures.

Figure 6A:
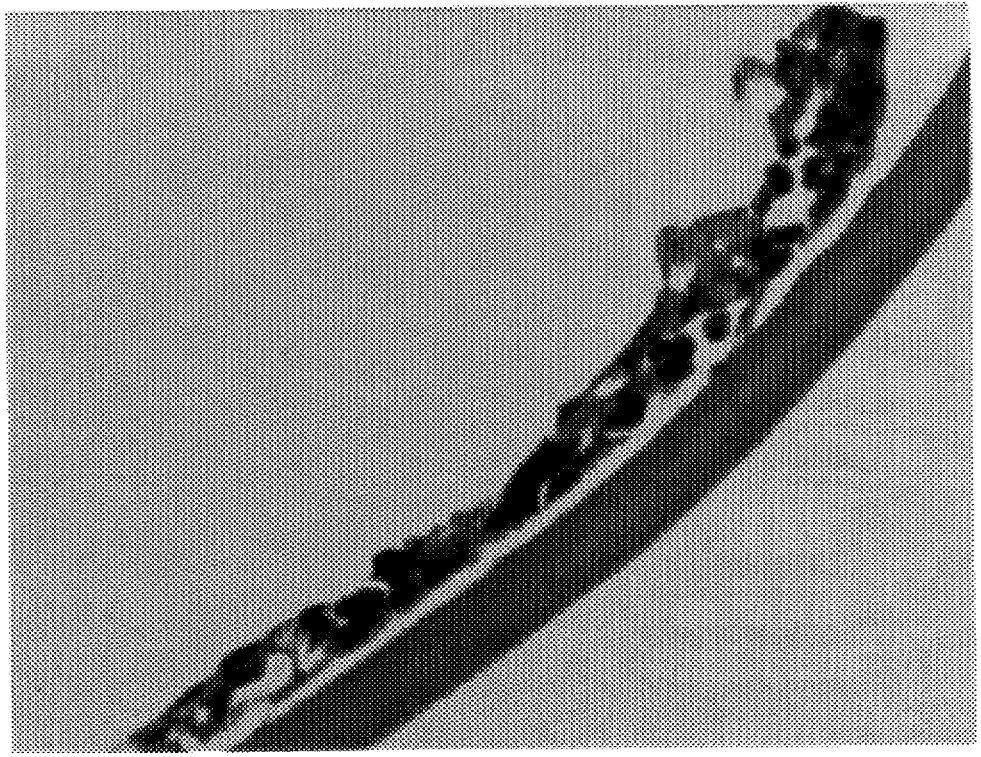
FIG. 6A is cells grown on collagen membrane.
Figure 6B:
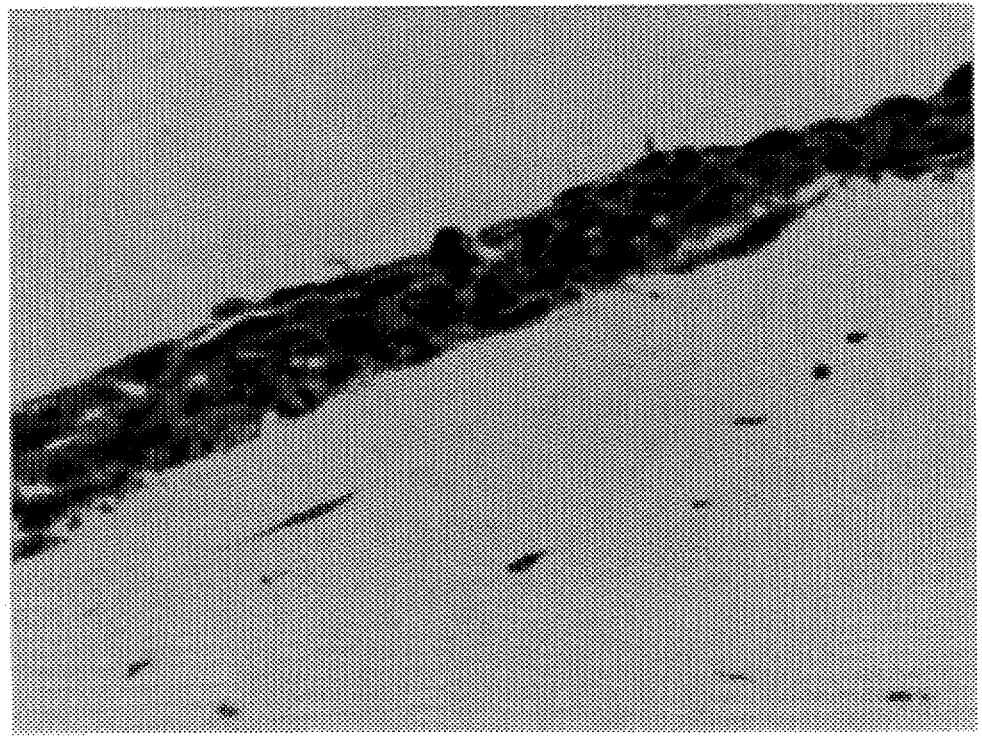
FIG. 6B is cells grown on a collagen matrix seeded with dermal fibroblasts.

When cultured upon collagen membranes (Cellagen™, ICN, Irvine, Calif.), or upon collagen matrices impregnated with fibroblasts (Organogenesis, Cambridge, Mass.) at air liquid interfaces, both control and HCE-T lines appeared to be tightly packed and more uniformly stratified than when cultivated on plastic, more closely approximating in vivo morphology. Control cultures achieved 4–6 cell layers of stratification while HCE-T developed 3–5 cell layers (FIG. 6a), and approximately 6 cell layers when grown on epidermal fibroblast impregnated collagen gels (FIG. 6b, Genesis System, Organogenesis, Cambridge, Mass.) as seen in cross section (Hematoxylin and Eosin, American Histology Labs, Gaithersburg, Md.).

Figure 8A:
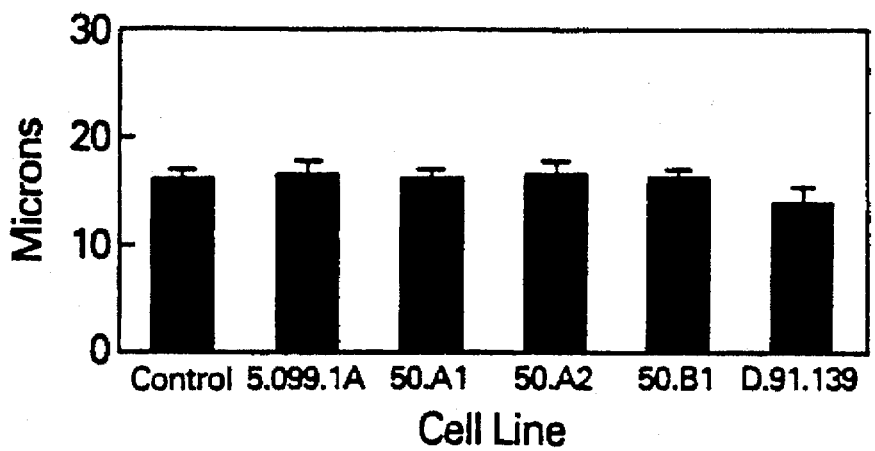
FIG. 8A is HCE cell diameter.

Although HCE-T were aneuploid and control cells were diploid, control cell diameter (16.6 μm±–0.3) was not different from HCE-T diameter (16.2 μm±–0.7) (FIG. 8a).

EXAMPLE 5

Indirect Immunofluorescence to Identify Viral and Corneal Proteins

Monoclonal anti-SV40 T antigen (Antibody 2, Oncogene Science, Inc. Uniondale, N.Y.) reacts with the 94 kD SV40 large T antigen (Harlow et al, 1981, *J. Virol.*, Vol. 39, pp. 861–869) and identifies SV40 infected cells. Monoclonal anti-cytokeratin hybridoma culture supernatants were kindly provided by Dr. T. T. Sun, NYU School of Medicine. Culture supernatant AE1 recognizes a group of acidic keratins including keratin 16, which is an acidic protein of 48 kD found in hyperproliferative epithelium, while AE3 reacts with keratin 12, a basic 64 kD cytokeratin found in all epithelial cells, and hybridoma culture supernatant AE5 is specific for keratin 3, a 64 kD protein found exclusively in differentiated corneal epithelial cells (Schermer et al, 1986, *J. Cell Biol.* Vol. 103, pp. 49–62). Monoclonal anti-vimentin (Oncogene Science, Uniondale, N.Y.) stains intermediate filaments found in cells derived from the mesenchymal gem layer (Osborn, 1985, *Ann. NY Acad. Sci.*, Vol. 455, pp. 669–681), migrating epithelial cells in vivo which are involved in wound repair, as well as in other epithelia propagated in vitro, including corneal epithelium (SunderRaj et al, 1992, *Cell Tissue Res.*, Vol. 267, pp. 347–356).

Cells were cultured for varying lengths of time in wells of FNC coated glass toxoplasmosis slides (Roboz, Rockville, Md.). Prior to staining, the medium was aspirated, and the slides were rinsed in PBS and fixed in ice-cold acetone:methanol (1:1) for 5 minutes in order to precipitate protein and solubilize lipids. After rehydration in PBS and air drying, the slides were incubated with 20 μL/well of antibody (1:50 in 3% BSA) or hybridoma culture supernatant in a humidified chamber for 60 minutes at 37° C. Control supernatant consisted of an anti-ELAM monoclonal antibody (Otsuka American, Rockville, Md.) raised against an endothelial cell-specific receptor. After two 15-minute washes in 1 liter PBS, the slides were dried for 2–3 minutes and fluorescein isothiocyanate (FITC)-conjugated goat anti-mouse antibody (1:200 in 3% BSA) was added to each well. Slides were incubated for 60 minutes at 37° C. After washing, slides were air dried, mounted using mounting medium for fluorescent microscopy (Kirkegaard and Perry, Gaithersburg, Md.) and sealed under a coverslip with clear nail polish to preserve the slide for photomicroscopy. Cells were viewed with a Zeiss epifluorescence microscope (Model ICM 405, 100 watt light source), using a 10× objective with either a 25× (0.60 NA) or a 40× lens (0.75 NA) and fluorescein filters. Fluorescent photomicrographs were prepared using 100 ASA Kodak color slide film or print film with a 30-second exposure time.

The pattern of reactivity of HCE-T was developed with antibodies specific for certain differentiated cell populations as shown in FIG. 9. Background levels of staining were negligible as seen in FIG. 9f. When propagated on tissue culture plastic, in the absence of fibroblasts, control cultures and most HCE-T lines reacted strongly with AE1 and AE3 (FIG. 9a–b). Approximately 5–10% of the cells in each culture also reacted with AE5 (FIG. 9c). This indicated the epithelial (AE3, FIG. 9b), hyperproliferative (AE1, FIG. 9a) and corneal (AE5, FIG. 9c) nature of the cells. Vimentin staining is seen in FIG. 9d.

Figure 9A:
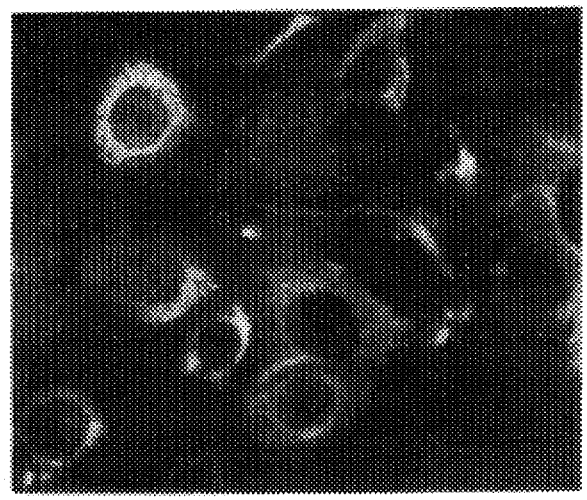
FIG. 9A is AE1 cytokeratin immunoreactivity.
Figure 9B:
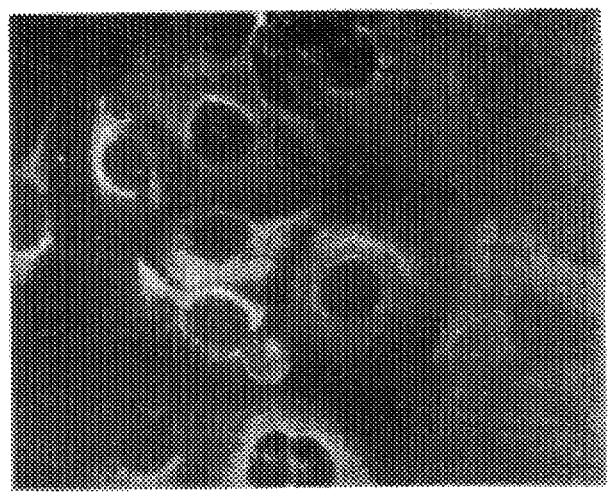
FIG. 9B is AE3 cytokeratin immunoreactivity.
Figure 9C:
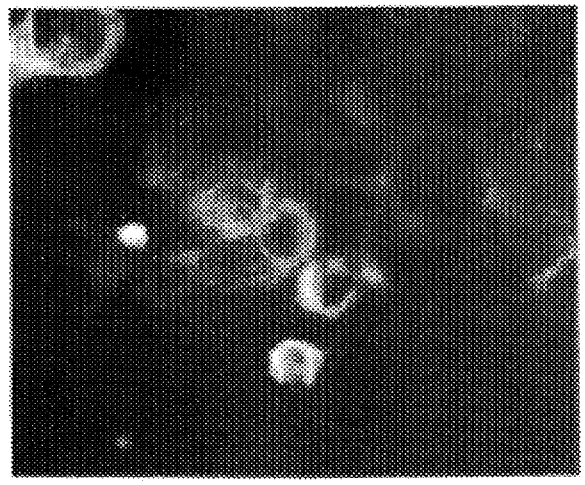
FIG. 9C is AE5 cytokeratin immunoreactivity.
Figure 9D:
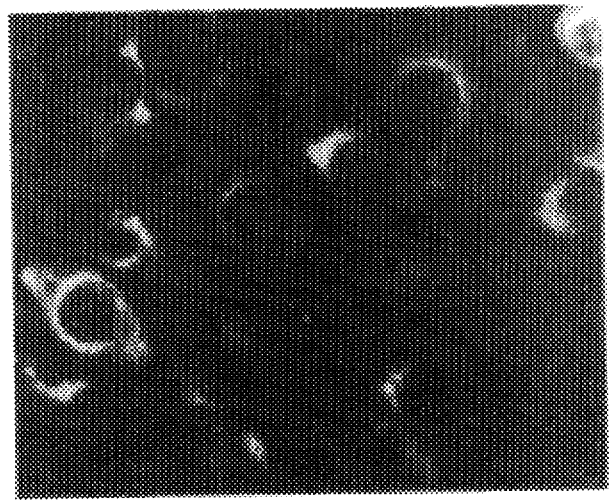
FIG. 9D is vimentin immunoreactivity.
Figure 9E:
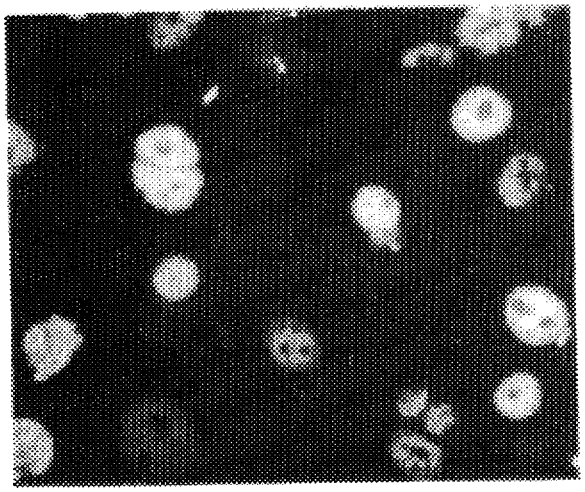
FIG. 9E is T antigen immunoreactivity.
Figure 9F:
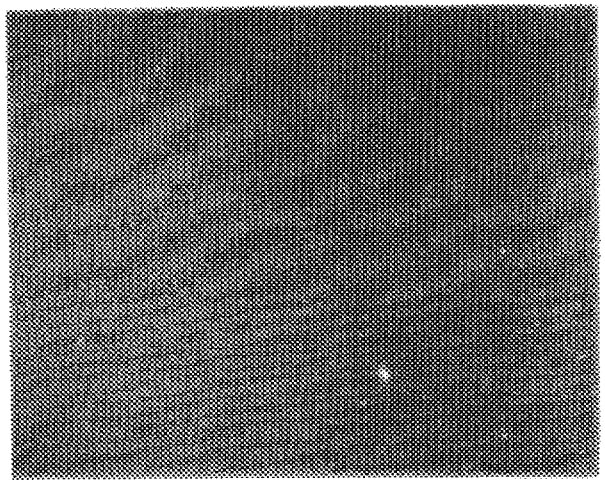
FIG. 9F is E-selectin immunoreactivity (negative control).
Figure 10A:
FIG. 10A is HCE-T propagated in serum-free medium and stained with FITC labeled AE3 antibody.
Figure 10B:
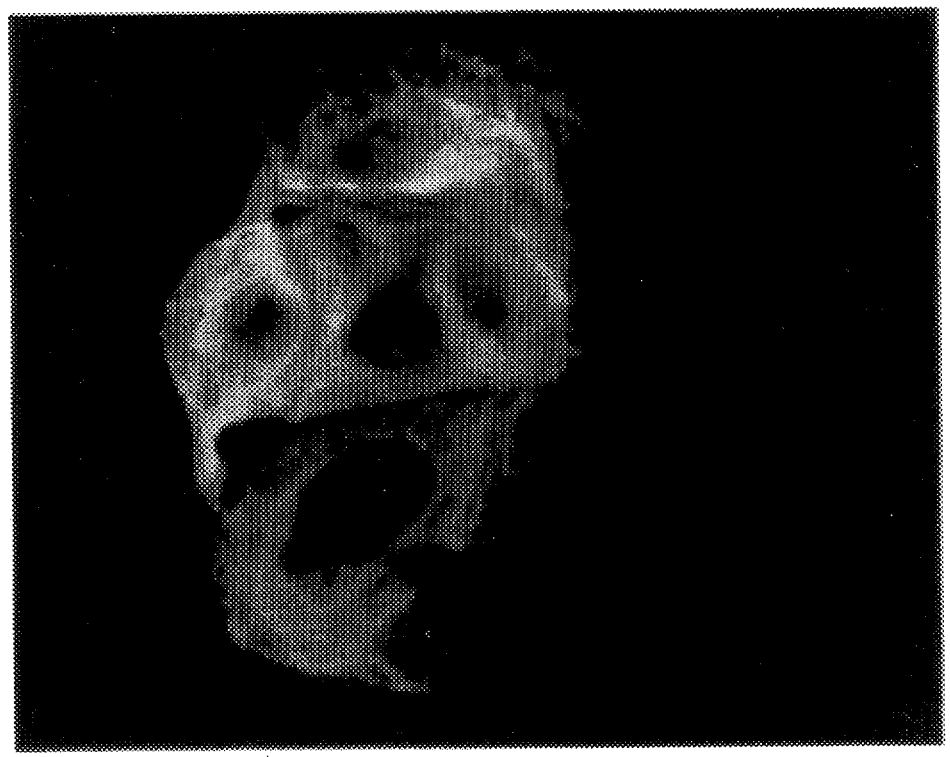
FIG. 10B is HCE-T propagated in medium supplemented with FBS (10%) and stained with FITC labeled AE3.
Figure 11A:
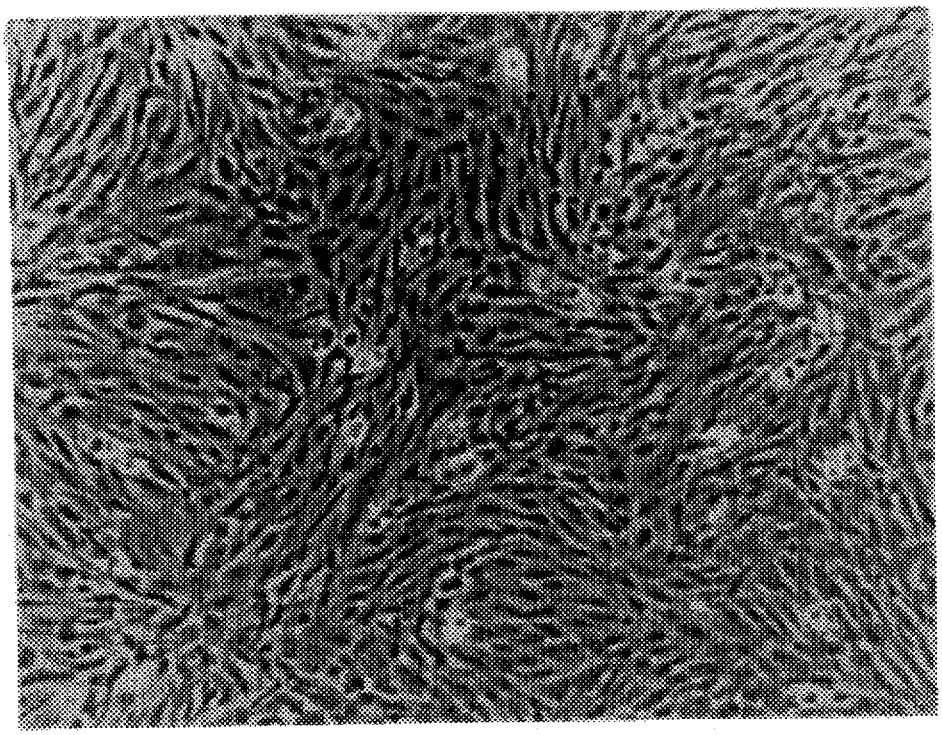
FIG. 11A is HCE-T (D91.139).
Figure 11B:
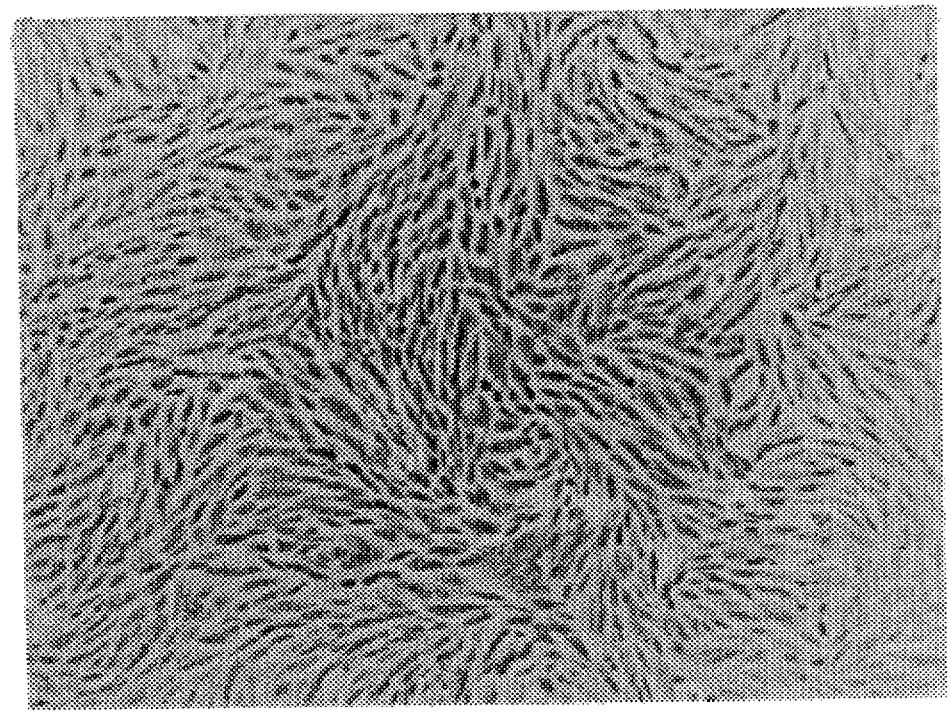
FIG. 11B is a SIRC cell line (rabbit corneal epithelial derived).
Figure 11C:
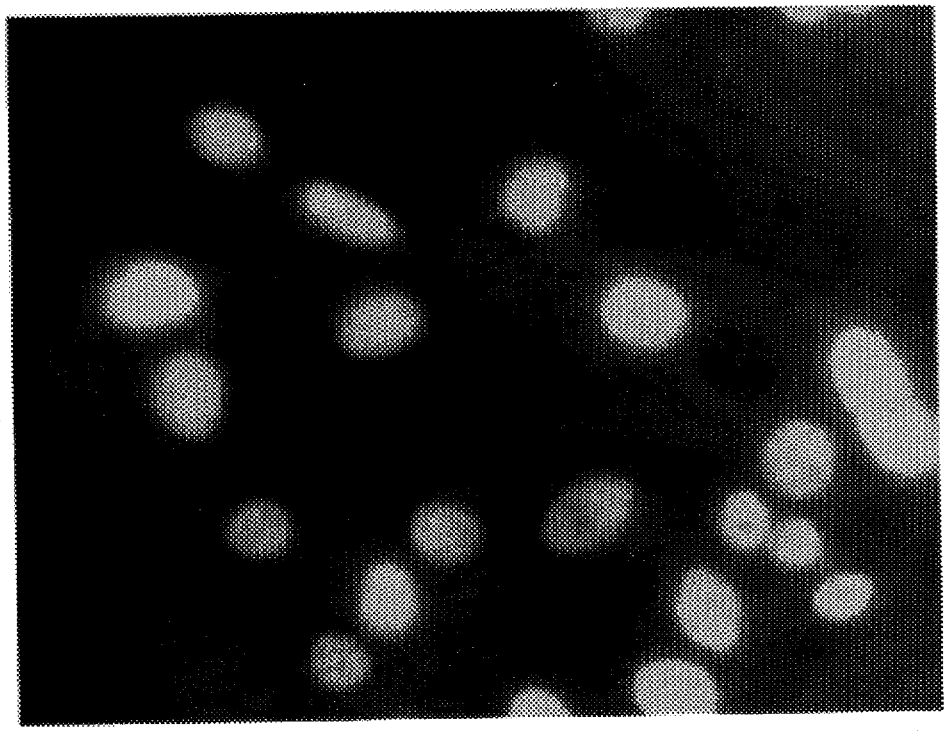
FIG. 11C is T antigen immunoreactive HCE-T line D91.139.
Figure 11D:
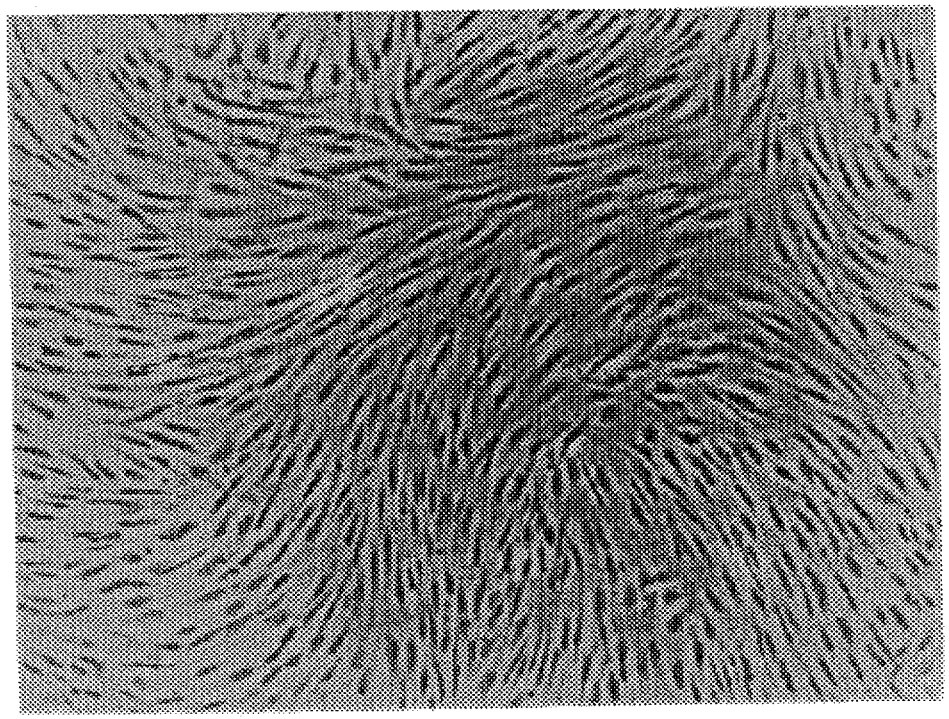
FIG. 11D is human corneal fibroblasts.

Cytokeratin staining was concentrated in the cytoplasm with a distinct network clearly visible. Both control and HCE-T reacted with anti-vimentin antibody, as is typical of corneal epithelium undergoing wound healing in situ. Characteristic T antigen staining, typified by an immunoreactive nucleus containing non-immunoreactive nucleoli, was seen only in the HCE-T (FIG. 9e). Addition of 10% FBS to the medium of both control and HCE-T lines resulted in an enhanced spreading of the cells on the substrate as clearly shown by the cytokeratin network (FIG. 10a,b). Cells in FIG. 10a were propagated in KGM, while those in FIG. 10b were propagated in 10% FBS. As illustrated in FIG. 11, one HCE-T line (D91.139) displayed a more fibroblastic-like morphology (FIG. 11a) and appeared remarkably similar to the SIRC cell line (FIG. 11b). Neither the SIRC or D91.139 reacted with AE3, AE1 or AE5 although D91.139 reacted with large T antibody (FIG. 11c). Both of these lines were morphologically distinct from human corneal fibroblasts (FIG. 11d) and epithelial cells.

EXAMPLE 6

Assay for Virus Production

To assess whether HCE-T lines were shedding virus into the culture supernatants, samples of culture supernatants from each line at multiple passages were examined for their ability to infect Vero cells (Rhim et al, 1981, *Proc. Natl.*

*Acad. Sci.* Vol. 78, pp. 313–317). Vero cells were plated in 6 well plates at 20% confluence in Earles MEM (EMEM) containing 5% FBS. Following 24 hours of incubation, medium was removed and 0.5 ml of "spent" filtered medium from each HCE-T culture was added along with 2.5 ml of fresh medium to a test well. Each plate contained one control well that received "spent" medium from an uninfected culture. Supernatants were tested immediately and also stored frozen for retesting at a later date. Each HCE-T line was tested at several passages (Table I). Passage numbers marked with an * were cytotoxic to Vero cells. Cultures were fed twice weekly for 21 days, at which time cytopathic effects (CPE) were scored. CPE is defined as any culture that appears different from the control.

TABLE I

| Viral Shedding | | | | | |
|---|---|---|---|---|---|
| 46 | 50 | 50.A1 | 50.A2 | 50.A3 | 50.B1 |
| 5* | 7* | 7 | 7 | 7* | 9 |
| 6* | 10* | 8 | 9 | 8* | 11 |
| 7 |  | 9 | 10 | 11* | 12 |
| 8 |  | 12 |  |  | 15 |
| 9 |  | 15 |  |  |  |
| 10 |  |  |  |  |  |
| 11 |  |  |  |  |  |

| 50.B2 | 50.B3 | 50.B4 | 50.C2 | 54 | 62 |
|---|---|---|---|---|---|
| 8* | 11 | 11* | 7 | 2* | 4* |
| 9 | 13 | 12* | 11 | 3 | 6* |
| 11 | 15 | 13 | 12 | 4 | 7* |
|  |  | 15 |  | 5 | 8* |
|  |  |  |  | 8 |  |
|  |  |  |  | 9 |  |

| 72 | 73 | 73.C1 | 88 | 89.A1 | 89.B1 |
|---|---|---|---|---|---|
| 4* | 5* | 6 | 5* | 6* | 8 |
| 5* | 8 | 8 | 8 | 7* |  |
|  |  |  |  | 8 |  |
|  |  |  |  | 9 |  |

| 89.B3 | 89.C1 | 5.099.1A |
|---|---|---|
| 8* | 7 | 17* |
| 9 | 10 | 27* |
| 12 |  |  |

*CPE observed in Vero cells

There was no correlation between the dose of virus to which the cells were exposed (multiplicity of infection) and the time at which viral shedding ceased. Shedding of whole virus into the culture supernatant ceased as early as $P_3$ in HCE-T line 54 and persisted at least until $P_{27}$ in HCE-T line 5.099.1A. Six of the 22 HCE-T lines generated by hybrid virus infection continued to shed virus and were not utilized (Table I).

Lines were developed from many different donors using virus infection (Ad12–SV40) (Table I) or transfection (pRSV-T). All investigations were done with lines that had ceased to shed virus into the culture supernatant. All lines were stored frozen in $N_2$ liquid and could be recovered as viable cells.

EXAMPLE 7

Kinetics, Saturation Density and Population Doubling Time Studies

The kinetics of growth were determined for control cultures and for each HCE-T line. Cells from each line ($1\times10^4$ cells/cm$^2$) were aliquoted into one 24 well cluster plate previously coated with FNC. After 24 hours, medium was exchanged and cultures were fed twice weekly during the course of the experiment. Cells were harvested with trypsin and counted at 24-hour intervals using a Coulter Counter, Model ZM (Coulter, Miami Lakes, Fla.). Population doubling time (PDT) was calculated from growth curves during log-phase growth as described by Jakoby and Pastan (*Methods in Enzymology*, 1979, Vol. LVIII, p. 150).

In order to determine how closely packed cells could become when grown submerged, cultures were established at $1\times10^4$ cells/cm$^2$ and allowed to propagate, with regular media changes, for 11 days. Cells were released with trypsin and counted using a Coulter Counter, Model ZM (Coulter, Miami Lakes, Fla.). Saturation density was calculated by dividing the total cell number by the area of the growth surface.

Figure 8B:
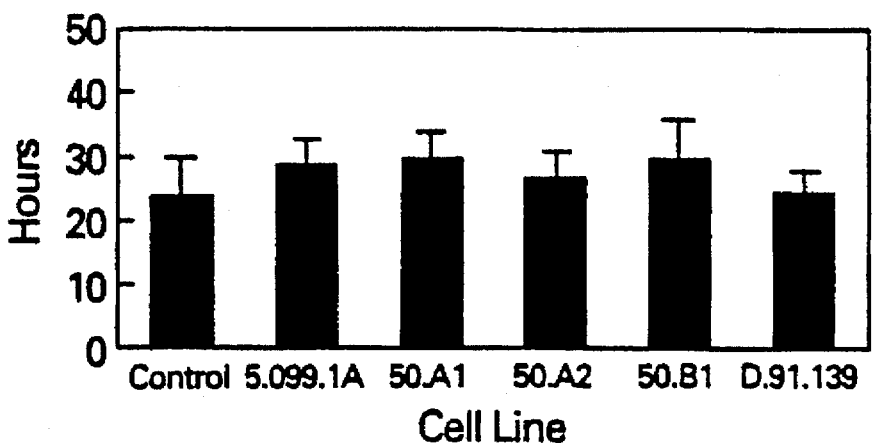
FIG. 8B is population doubling time.
Figure 8C:
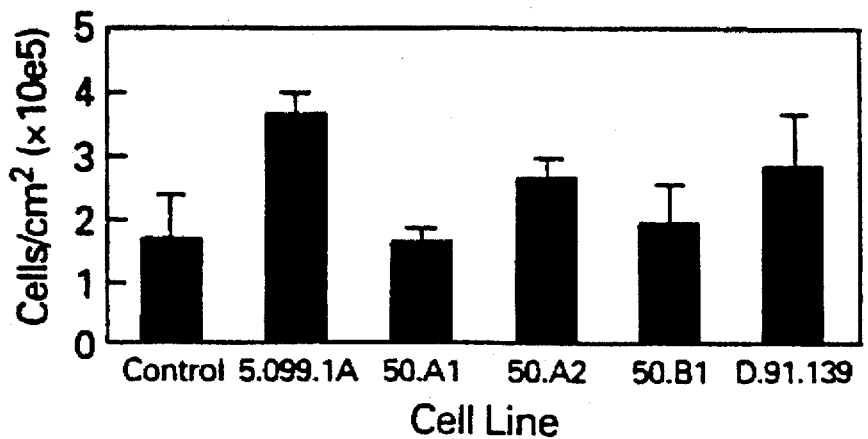
FIG. 8C is saturation density.

Seeding efficiency was approximately 85% for both control and HCE-T lines. One day after plating, about 50% of the cells attached. Log phase growth generally occurred between days 2 and 6, and by day 7, growth began to plateau. Population doubling times (FIG. 8b) determined on plastic growth surface during log phase growth revealed no difference between control cultures and lines. Doubling times of control cultures ranged from 24 to 26 hours compared to 25 to 30 hours for the HCE-T lines. Control cultures had a saturation density (SD) of $1.7\times10^5$ cells/cm$^2$ while each HCE-T line had a characteristic SD ranging from 1.7 to $3.7\times10^5$ cells/cm$^2$ (FIG. 8c).

EXAMPLE 8

Soft Agar Cloning of Transformed Cells

Autoclaved agar (0.9%, Difco, Detroit, Mich.) was dissolved in Dulbecco's Minimal Essential Medium (DMEM) containing 20% FBS, aliquoted (5 ml) into sterile 60 mm Petri plates and incubated at 37° C. overnight. This base was overlaid with $1\times10^5$ HCE-T or control cells in 0.36% agar (2.0 ml). Plates were incubated at 37° C. for 4 weeks at which time colony formation was scored. Only colonies containing more than 4 cells were counted. Negative controls were non-virus exposed corneal epithelial cells derived from primary cultures of donor tissue while positive controls were mos oncogene transformed endothelial cells (kindly provided by Dr. Michael Seidman, Otsuka America, Rockville, Md.).

As shown in Table II, control cultures do not form colonies in soft agar, indicating that substrate attachment was a prerequisite to growth. Nine of the immortalized lines tested did not form colonies in semi-solid agar, but two lines (50.B1 and 50.C2) did express the ability to develop small, disperse colonies. The colonies developed in 50.B1 and 50.C2 ranged from 0.05–0.08 mm in diameter, indicating a moderate degree of anchorage independence. A mos transformed line, which served as the positive control, developed 40-fold more colonies with each colony being 4-fold greater in diameter, reflecting its transformed phenotype which was highly anchorage independent.

TABLE II

| Attachment Dependent Growth | | |
|---|---|---|
| Cell Line | Growth in Agar | # Colonies in 10 squares |
| Control (−) | − | 0 |
| Control (+) | +++ | 253 |

TABLE II-continued

Attachment Dependent Growth

| Cell Line | Growth in Agar | # Colonies in 10 squares |
|---|---|---|
| 7.107pRSV-T | − | 0 |
| 50.A1 | − | 0 |
| 50.A2 | − | 0 |
| 50.B1 | + | 8 |
| 50.B2 | − | 0 |
| 50.B3 | − | 0 |
| 50.C2 | + | 15 |
| 89.B3 | − | 0 |
| 89.C1 | − | 0 |

+ 0.05–0.10 mm diameter
++ 0.15–0.20 mm diameter
+++ >0.25 mm diameter

EXAMPLE 9

Karyotype and Isozyme Analysis

Figure 7A:
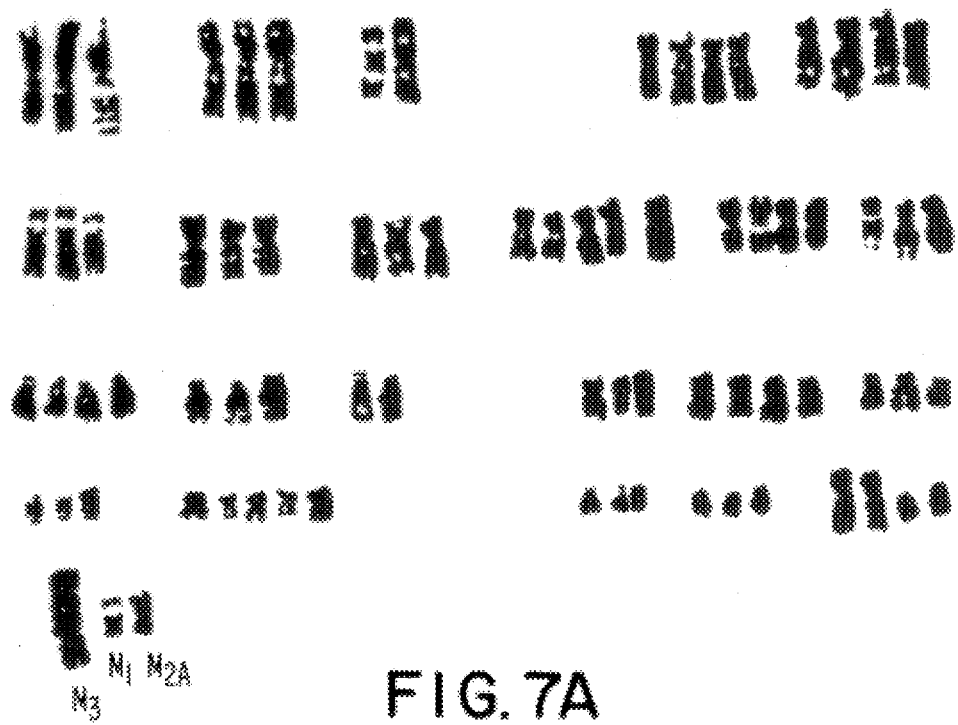
FIG. 7A is line 50.C2.
Figure 7B:
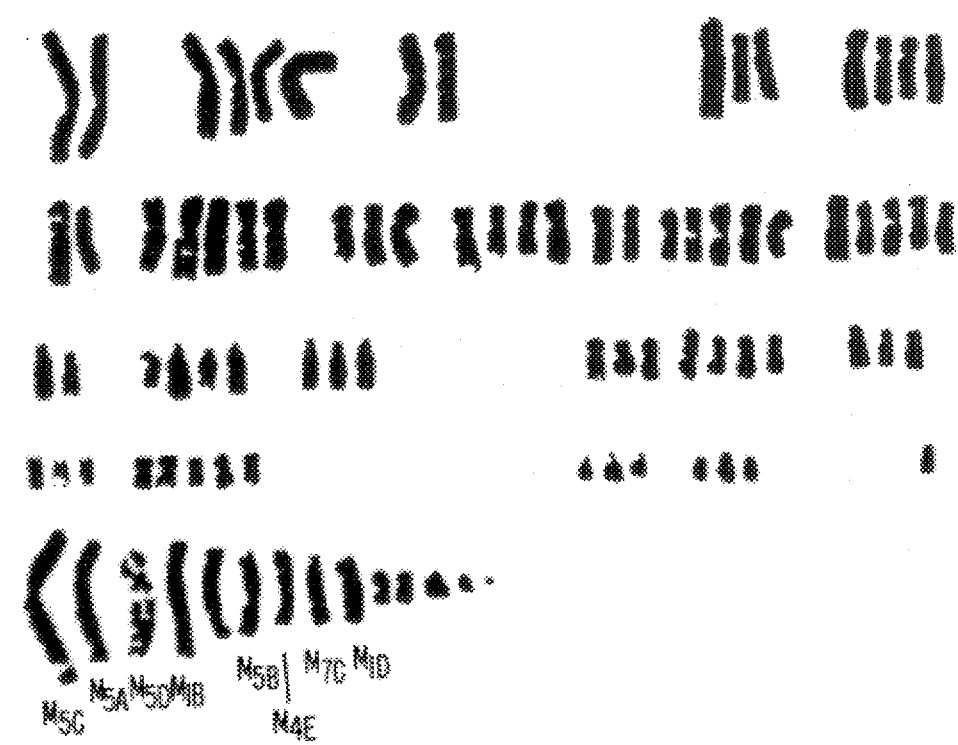
FIG. 7B is line 50.B1 (deposited with the American Type Culture Collection (ATCC), 12301 Parklawn Drive, Rockville, Md. 20852, USA on Sep. 23, 1992, and given ATCC deposit number CRL11135).

For each cell strain, chromosomes were counted in 40 to 145 metaphase spreads, and a minimum of 7 Giemsa-banded karyotypes were examined. Karyotypes of two of the HCE-T lines, 50.B1 and 50.C2, which were generated from the same donor, were analyzed (FIG. 7). Although they both contained the Y chromosome of the donor, different marker chromosomes were detected in the two cultured lines, indicating that they had become genetically different from one another during propagation in vitro. The karyotypes of the control cultures were near-diploid while the karyotypes of the HCE-T were aneuploid and heteroploid (FIG. 7a–b), as is typical of virally immortalized lines.

The human origin of all the lines examined was confirmed by isozyme profile. The following seven enzymes were used for species identification by isozyme phenotype frequencies: lactate dehydrogenase (LDH), glucose-6-phosphate dehydrogenase (G6PD), purine nucleoside phosphorylase (NP), malate dehydrogenase (MDH), mannose phosphate isomerase (MPI), aspartate aminotransferase (AST) and peptidase B (PEPB). The seven enzymes used to calculate the phenotypic frequency product were G6PD, phosphoglucomutase-1 (PGM1), phosphoglucomutase-3 (PGM3), esterase D (ESD), malic enzyme, mitochondrial (Me-2), adenylate kinase (AK-1) and glyoxylase-1 (GLO-1).

The phenotypic frequency product was determined to be 0.00116 (Table III), indicating that less than 1% of the cell lines might be expected to have an isozyme phenotypic profile identical to this.

TABLE III

Isozyme Phenotype

|  | 50.B1 | 50.C2 |
|---|---|---|
| LDH | human | human |
| G6PD | A | A |
| PGM1 | 1 | 1 |
| PGM3 | 2 | 1 |
| ESD | 1 | 1 |
| Me-2 | 1–2 | 1–2 |
| AK-1 | 1 | 1 |
| GLO-1 | 2 | 2 |

EXAMPLE 10

Transepithelial Permeability Measurements

Cells were seeded at $1.5 \times 10^5$ cells/9 mm collagen membrane and propagated submerged in 1.5 ml of medium for 3 days. During day 4, cells were refed with 1 ml of medium, essentially bringing the cells to the air liquid interface. Measurements were made essentially as described by Tchao (*Alternative Methods of Toxicology*, 1988, Vol. 6, pp. 271–283, Goldberg, A. M., ed. Mary Ann Liebert, Inc., New York, N.Y.) on day 6. Briefly, 200 ml of sterile Na-fluorescein (0.02%) was added to the apical surface of the cells and incubated at 37° C. for 30 minutes. 1 ml of culture fluid from the basal surface of the cells (medium in the well bathing the underside of the membrane) was diluted 1:1 in PBS and read at 490 nm in a spectrophotometer (Hewlett-Packard, Palo Alto, Calif.), or read undiluted at 490 nm in an ELISA plate reader (Dynatech, Chantilly, Va.).

Figure 12:
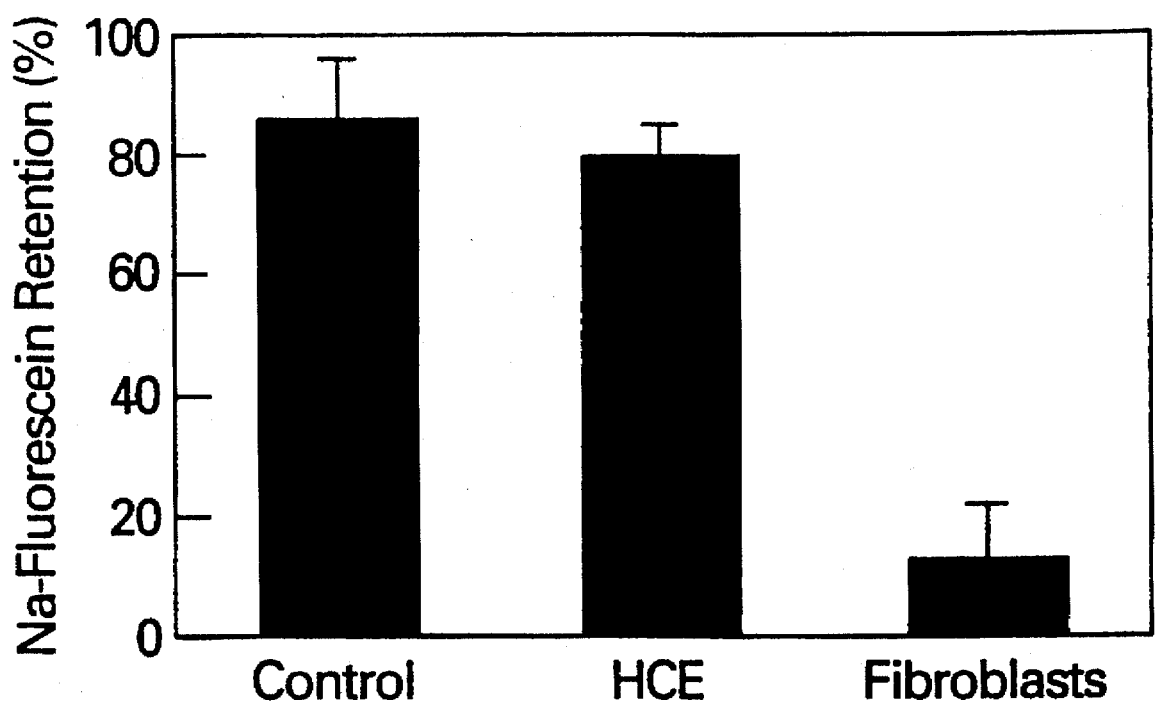
FIG. 12 shows dye diffusion across HCE-T epithelium reflecting transepithelial permeability.
Figure 14A:
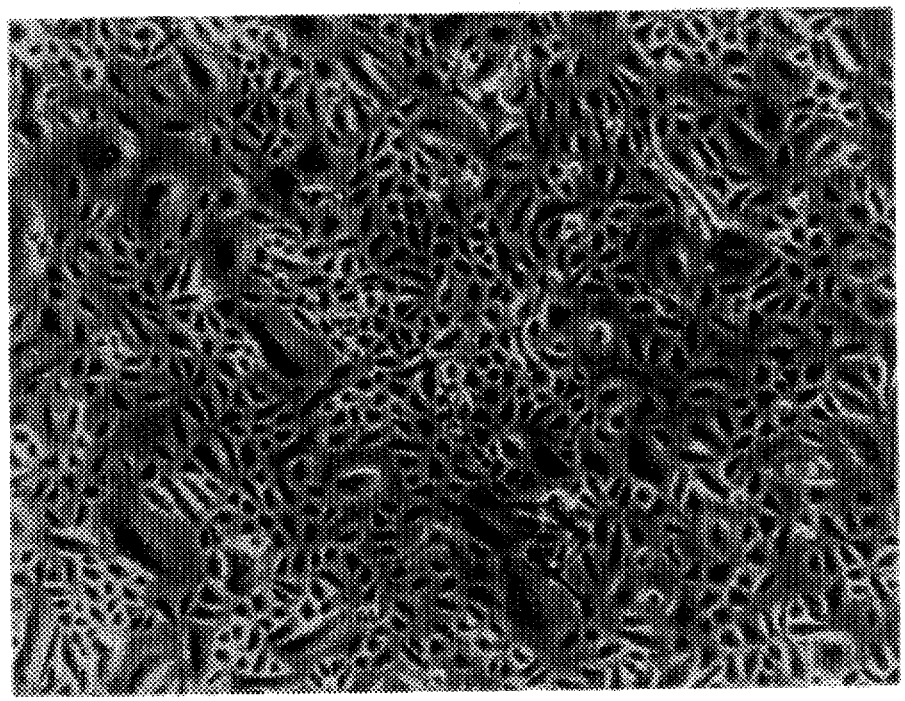
FIG. 14a shows HCE (primary culture) on fibronectin/collagen coated flash.
Figure 14B:
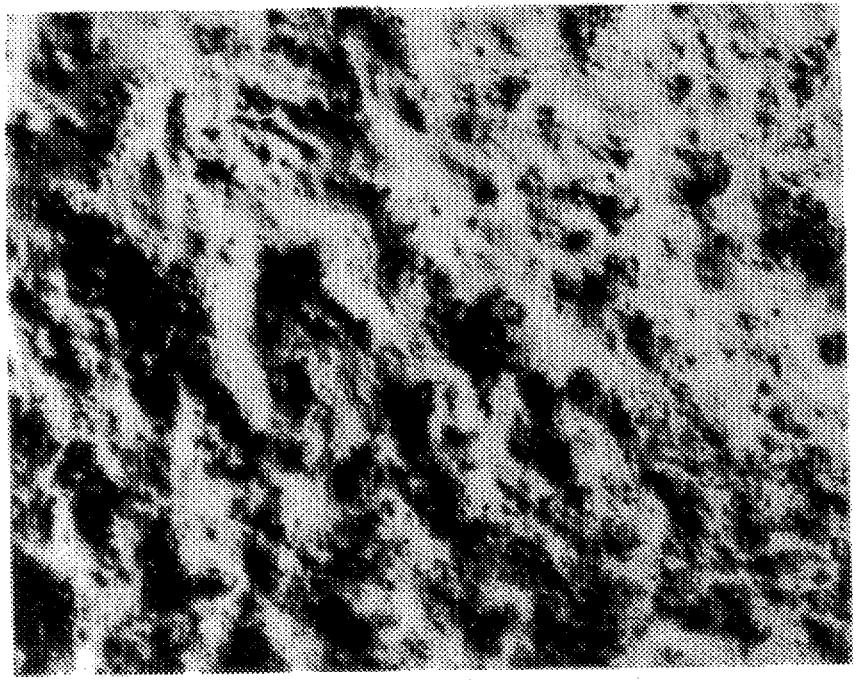
FIG. 14b shows HCE (primary culture) at air/liquid interface on Cellagen™ discs.
Figure 14C:
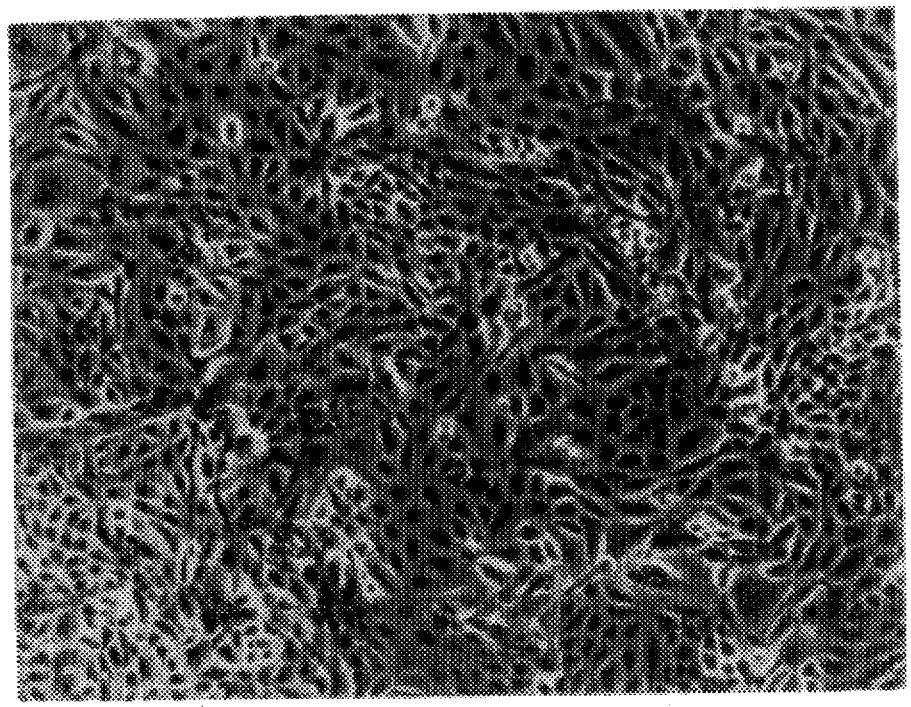
FIG. 14c shows cell line 10.014 pRSV-T on fibronectin/collagen coated flasks.
Figure 14D:
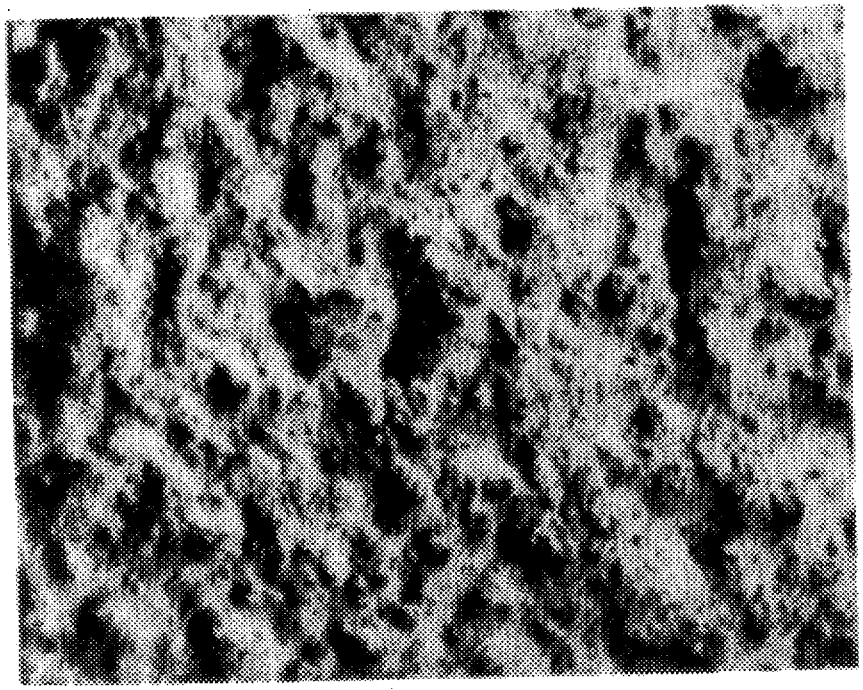
FIG. 14d shows cell line 10.014 pRSV-T at air/liquid interface on Cellagen™ discs.

Corneal control cells and HCE-T lines cultured on collagen membranes at the air-liquid interface retarded the flow of Na-fluorescein by 80–95%. Cultures of corneal fibroblasts were not able to retard the flow of the ionic dye marker beyond 15% (FIG. 12).

EXAMPLE 11

Properties of Cells with Unexpectedly Superior Characteristics

Two cell lines obtained by transfection with plasmid pRSV-T had surprisingly superior characteristics compared to other similarly obtained cell lines. Cell lines 10.014 pRSV-T and 2.040 pRSV-T were able to be passaged twenty or more times. These cells exhibited AE5 reactivity and favorable resistance values (FIG. 13). Photomicrographs of one of these cell lines, 10.014, are shown in FIG. 14.

While the invention has been described and illustrated herein by references to various specific material, procedures and examples, it is understood that the invention is not restricted to the particular material combinations of material and procedures selected for that purpose. Numerous variations of such details can be implied as will be appreciated by those skilled in the art.

What is claimed is:

1. An immortalized human corneal epithelial cell line selected from the group consisting of cell line 10.014 and cell line 2.040.

2. The cell line of claim 1, wherein said cell line has been infected with a virus.

3. The cell line of claim 2, wherein said virus is an SV40 virus.

4. The cell line of claim 3, wherein said SV40 virus is a hybrid virus.

5. The cell line of claim 4, wherein said hybrid virus is Adeno12-SV40.

6. The cell line of claim 1, wherein said cell line has been transfected with a plasmid.

* * * * *